US012781274B2

(12) United States Patent
Lin et al.

(10) Patent No.: US 12,781,274 B2
(45) Date of Patent: Nov. 3, 2026

(54) REPLICASE CYCLING REACTION (RCR) AND THE RELATED RdRP-BINDING SITE DESIGNS THEREOF

(71) Applicants: Shi-Lung Lin, Arcadia, CA (US); Sam Lin, Arcadia, CA (US)

(72) Inventors: Shi-Lung Lin, Arcadia, CA (US); Sam Lin, Arcadia, CA (US)

( * ) Notice: Subject to any disclaimer, the term of this patent is extended or adjusted under 35 U.S.C. 154(b) by 633 days.

(21) Appl. No.: 18/479,983

(22) Filed: Oct. 3, 2023

(65) Prior Publication Data

US 2024/0093286 A1 Mar. 21, 2024

Related U.S. Application Data

(63) Continuation-in-part of application No. 17/489,357, filed on Sep. 29, 2021, now Pat. No. 12,570,977, and a continuation-in-part of application No. 17/648,336, filed on Jan. 19, 2022, now Pat. No. 12,590,329, and a continuation-in-part of application No. 17/648,340, filed on Jan. 19, 2022, now abandoned, and a continuation-in-part of application No. 18/156,231, filed on Jan. 18, 2023, now Pat. No. 12,618,068.

(60) Provisional application No. 63/429,150, filed on Dec. 1, 2022, provisional application No. 63/530,687, filed on Aug. 3, 2023.

(51) Int. Cl.

| | |
|---|---|
| ***C12N 15/11*** | (2006.01) |
| ***A61K 31/713*** | (2006.01) |
| ***C12N 15/10*** | (2006.01) |
| ***C12Q 1/686*** | (2018.01) |

(52) U.S. Cl.

CPC ............ *C12Q 1/686* (2013.01); *A61K 31/713* (2013.01); *C12N 15/1096* (2013.01)

(58) Field of Classification Search

None

See application file for complete search history.

(56) References Cited

U.S. PATENT DOCUMENTS

| | | | |
|---|---|---|---|
| 7,662,791 | B2 | 2/2010 | Lin et al. |
| 8,080,652 | B2 | 12/2011 | Lin et al. |
| 8,372,969 | B2 | 2/2013 | Mng et al. |
| 8,609,831 | B2 | 12/2013 | Lin et al. |
| 11,291,635 | B2 | 4/2022 | Geall et al. |
| 11,504,421 | B2 | 11/2022 | Blair et al. |
| 11,510,973 | B2 | 11/2022 | Blair et al. |
| 2023/0242958 | A1 | 8/2023 | Lin et al. |

FOREIGN PATENT DOCUMENTS

| | | | |
|---|---|---|---|
| WO | 02092774 | A2 | 11/2002 |

OTHER PUBLICATIONS

Aasen et al., "Isolation and cultivation of human keratinocytes from skin or plucked hair for the generation of induced pluripotent stem cells," Nature Protocols, 2010, vol. 5, No. 2, pp. 371-382.

Ahn et al., "Biochemical characterization of a recombinant SARS coronavirus nsp12 RNA-dependent RNA polymerase capable of copying viral RNA templates," Archives of Virology, 2012, vol. 157, pp. 2095-2104.

Bloom et al., "Self-amplifying RNA vaccines for infectious diseases," Gene Therapy, 2021, vol. 28, pp. 117-129.

Hillen et al., "Structure of replicating SARS-CoV-2 polymerase," Nature, Aug. 6, 2020, vol. 584, 13 pages.

Hyde et al., "The 5' and 3' ends of alphavirus RNAs—Non-coding is not non-fuctional," Virus Research, 2015, vol. 206, pp. 99-107.

Lin et al., "cDNA Library Construction Using in Vitro Transcriptional Amplification," in: Methods in Molecular Biology, vol. 221: Generation of cDNA Libraries: Methods and Protocols, Ed. S.-Y. Ying, 2003, Humana Press, Inc., Totowa, NJ, pp. 93-101.

Lin et al., "Mir-302 reprograms human skin cancer cells in pluripotent ES-cell-like state," RNA, 2008, vol. 14, pp. 2115-2124.

Lin et al., "Regulation of somatic cell reprogramming through inducible mir-302 expression," Nucleic Acids Research, 2011, vol. 39, No. 3, pp. 1054-1065.

Mcdowell et al., "Determination of Intrinsic Transcription Termination Efficiency by RNA Polymerase Elongation Rate," Science, Nov. 4, 1994, vol. 266, pp. 822-825.

Takahashi et al., "Induction of Pluripotent Stem Cells from Mouse Embryonic and Adult Fibroblast Cultures by Defined Factors," Cell, Aug. 25, 2006, vol. 126, pp. 663-676.

*Primary Examiner* — Ekaterina Poliakova-Georgantas
(74) *Attorney, Agent, or Firm* — ArentFox Schiff LLP

(57) ABSTRACT

This invention relates to a novel composition of RNA/mRNA medicines and/or vaccines produced by using Replicase/RNA-dependent RNA polymerase (RdRP)-mediated RNA Cycling Reaction (RCR). This RCR-amplifiable RNA/mRNA composition comprises at least a replicase/RdRP-binding site (RdRP-BS) in the 5'-end or 3'-end, or both, of a desired RNA sequence of interest, to form a self-amplifying RNA/mRNA (samRNA) platform. The samRNA platform so obtained is useful for designing and developing a variety of self-amplifying RNA/mRNA (samRNA) constructs, of which the desired RNA sequences may include, but not limited to, antisense oligonucleotide RNA (aRNA; ASO), small interfering RNA (siRNA), short hairpin RNA (shRNA), microRNA (miRNA)/miRNA precursor (pre-miRNA), long non-coding RNA (lncRNA), and/or messenger RNA (mRNA), or a combination thereof. The present RdRP-BS designs in said samRNA are derived or modified from the identified RdRP-BS motifs of coronavirus (e.g. SARS-CoV-2-associated viruses) and/or hepatitis C virus (HCV) in either single-stranded or double-stranded conformation, or a combination thereof.

18 Claims, 11 Drawing Sheets

Specification includes a Sequence Listing.

SARS-CoV-2 S protein expression after samRNA transfection hematoxylin stain (background)

iPSCs after samRNA-eGFP transfection iPSCs (bright field)

REPLICASE CYCLING REACTION (RCR) AND THE RELATED RdRP-BINDING SITE DESIGNS THEREOF

PRIORITY

The present invention claims priority to U.S. Provisional Patent Applications No. 63/429,150 filed on Dec. 1, 2022, and No. 63/530,687 filed on Aug. 3, 2023, both of which are entitled "Novel Replicase Cycling Reaction (RCR) and The Related SamRNA Designs Thereof". In addition, the present application is a continuation-in-part (CIP) application of the U.S. patent application Ser. No. 17/489,357 filed on Sep. 29, 2021, which is entitled "Novel mRNA Composition and Production Method for Use in Anti-Viral and Anti-Cancer Vaccines". The present application is also a CIP application of the U.S. patent application Ser. No. 17/648,336 filed on Jan. 19, 2022, which is entitled "Novel Replicase Cycling Reaction (RCR)". Moreover, the present application is a CIP application of the U.S. patent application Ser. No. 17/648,340 filed on Jan. 19, 2022, which is entitled "Novel RNA Composition and Production Method for Use in iPS Cell Generation". Furthermore, the present application is a CIP application of the U.S. patent application Ser. No. 18/156,231 filed on Jan. 18, 2023, which is entitled "Novel Replicase Cycling Reaction (RCR) and The Related SamRNA Designs Thereof". All aforementioned six prior patent applications are hereby incorporated by reference as if fully set forth herein.

REFERENCE TO AN ELECTRONIC SEQUENCE LISTING

The contents of the electronic sequence listing (sequencelisting.xml; Size: 27,312 bytes; and Date of Creation: Oct. 2, 2023) is herein incorporated by reference in its entirety.

FIELD OF INVENTION

This invention generally relates to a novel non-replicon-based self-amplifying RNA/mRNA (samRNA) composition capable of being produced and amplified by using a methodology of Replicase- and/or RNA-dependent RNA polymerase (RdRP)-mediated Cycling Reaction (RCR). Particularly, the present invention is a novel samRNA composition comprises at least a defined replicase/RdRP-binding site (RdRP-BS) in the 5'-end or 3'-end region, or both, of a desired RNA sequence, including but not limited to antisense oligonucleotide RNA (aRNA; ASO), small interfering RNA (siRNA), double-stranded RNA (dsRNA), short hairpin RNA (shRNA), microRNA (miRNA)/microRNA precursor (pre-miRNA), long noncoding RNA (lncRNA), and/or messenger RNA (mRNA), or a combination thereof. The conformation of said samRNA composition and the related desired RNA sequence can be single strand or double strand, or a combination thereof. Conceivably, the present invention can be used to generate a variety of samRNA constructs, which are useful not only for designing and developing a variety of RNA/mRNA-based vaccines and medicines but also for generating the mRNA-associated proteins, peptides, and/or antibodies using an in-vitro, in-cell and/or in-vivo translation system. Notably, the present RdRP-BS designs in said samRNA composition are derived or modified from the identified RdRP-BS of coronavirus (e.g. COVID-19/SARS-CoV-2-associated viruses) and/or hepatitis C virus (HCV) in either single-stranded or double-stranded conformation, or both.

BACKGROUND

Prior polymerase chain reaction (PCR) is a method of using thermostable DNA polymerases to amplify double-stranded DNA sequences from DNA templates, no involvement of any RNA material. Unlike PCR, the presently invented replicase/RdRP-mediated cycling reaction (RCR) uses viral replicases and/or RNA-dependent RNA polymerases (RdRP) to amplify desired single-stranded and/or double-stranded RNA/mRNA sequences from pre-designed samRNA platform templates, no necessity of any DNA template or DNA polymerase. Hence, PCR and RCR are totally different methods and clearly not comparable to each other. Accordingly, previous PCR studies are not related to RCR.

Lin et al. had first reported RCR in year 2002 (WO2002/092774 to Lin). Lin found that a special design of 5'-cap/5'-end-capture primers can be used to trigger viral and/or bacteriophage replicase-mediated RNA amplification from a pre-designed single-stranded or double-stranded RNA/mRNA template. Mechanistically, this primer-dependent RCR mimics the process of certain viral/bacteriophage replication, but not representing that of all other kinds of viruses. Particularly, the requirement of specific 5'-cap or 5'-end-capture primers limits its use because many RNA species do not carry 5'-cap molecules. Also, the linked 5'-cap-capture molecules may cause contamination to the resulting RNA/mRNA products. For serving RNA medicines and/or mRNA vaccines, this contamination is problematic because removal of the 5'-cap-capture molecules from the RNA/mRNA products is tedious and may lead to RNA degradation. Hence, a new RCR method without using any 5'-cap/5'-end-capture primer is highly desired.

In year 2012, Ahn et al reported a pair of 5'- and 3'-UTR RNA-dependent RNA polymerase (RdRP)-binding regions isolated from severe acute respiratory syndrome coronavirus (SARS-CoV-1) (Ahn et al., *Arch. Virol.* 157:2095-2104, 2012). This pair of SARS-CoV-1 RdRP-binding regions consists of minimal 36~39-nucleotide (nt)-long hairpin-like stem-loop RNA structures, respectively, which are however not compatible with conventional PCR or in-vitro transcription (IVT) methods due to their lengthy and highly structured sequences. Logically, in order to prevent tedious and costly replicon/plasmid preparations in the manufacture process, a combined methodology of polymerase chain reaction and in-vitro transcription (PCR-IVT; FIG. 1) is often used for incorporating a small motif sequence (e.g. RdRP-BS) into the desired RNA sequence of interest, so as to generate an amplifiable RNA/mRNA template, or called a self-amplifying RNA/mRNA (samRNA) platform (as shown in FIG. 1; U.S. Pat. Nos. 7,662,791, 8,080,652, 8,372,969, and 8,609,831 to Lin; Lin et al., *Methods Mol Biol.* 221:93-101, 2003). Nevertheless, Ahn's finding is not compatible with PCR-IVT because the reported SARS-CoV-1 5'-/3'-UTR RdRP-binding regions are too lengthy and too structural to be used in either PCR or IVT. Also, based on prior McDowell's study (McDowell et al., *Science* 266:822-825, 1994), it suggests that a hairpin-like stem-loop structure resembles the intrinsic termination signal of prokaryotic RNA polymerase-mediated transcription. Moreover, a skilled person in the field of biotechnology must know that a PCR primer should not contain any hairpin-like stem-loop structure, which hinders the annealing and extension steps of PCR. As a result, Ahn's RdRP-binding regions can not be used for preparing amplifiable RNA/mRNA templates, leading to no suitable template for RCR-like RNA amplification. Moreover, Ahn's finding is limited to SARS-CoV-1 RdRP, not else. For COVID-19 SARS-CoV-2 RdRP, Ahn's finding is not useful because the reported essential sequences of Ahn's SARS-CoV-1 RdRP-binding regions are different from those of the identified SARS-CoV-2 or HCV RdRP-binding sites. Because the replication mechanisms of SARS-CoV-1 and SARS-CoV-2 viruses are slightly different (for example, SARS-CoV-1 is more depending on primer-dependent RNA synthesis, while SARS-CoV-2 is more relied on de novo RNA synthesis), the essential RdRP-binding motifs of SARS-CoV-2 have been found to be more compact and less structural than the reported SARS-CoV-1 RdRP-binding regions.

In recent years, several samRNA-like self-replicating RNA (saRNA) designs have been reviewed by Bloom et al. (*Gene Therapy* 28:117-129, 2021), using alphaviral RdRP and its 3'-end binding/recognition site, a 19~24-nucleotide (nt)-long 3'-conserved sequence element called 3'-CSE. Yet, alphaviral 5'-CSE is found to interact with viral NSP2 and 3, but not NSP4 (the core RdRP unit), and requires some host cell factors to initiate viral replication, indicating that 5'-CSE is not a real RdRP-binding site (Hyde et al., *Virus Res.* 206:99-107, 2015). As a result, neither concept nor practical detail of any RCR-like protocol can be provided due to lack of any defined 5'-end RdRP-binding/recognition site. Although Bloom's review methods may not use any 5'-cap/5'-end-capture primer, the reported 3'-CSE is too long and too structural to be placed in a PCR primer and thus not useful for RCR-amplifiable template preparation, suggesting that the proposed 3'-CSE-containing saRNA/samRNA is clearly not compatible with either PCR-IVT or RCR methods. Alternatively, these 3'-CSE-containing saRNA/samRNA designs use vector (e.g. replicon/plasmid)-based amplification methods to produce and amplify the designed saRNA constructs in transfected cells or bacteria. Nevertheless, none of the 3'-CSE-containing saRNA constructs have ever been successfully tested in RCR or any other similar method in vitro. Because these replicon-based saRNA designs adopt a large portion of modified viral RNA genomes, but not specifically defined RdRP-binding sites, it is noted that these replicon-based saRNA constructs are different from and thus not comparable to the samRNA compositions of the present invention, using specific, well defined RdRP-binding site (RdRP-BS) motifs. Also, replicon-based saRNA amplification is required to be done in cells using some host cell factors, making RCR in vitro impossible. More problematically, the proposed 3'-CSE is recognized only by alphaviral replicase/RdRP enzymes, which consist of at least four distinct subunits and are not commercially available, leading to a huge obstacle in the development of its related RCR-like technology. Given that different viruses possess different replicase/RdRP features, it is desirable to search and utilize other better kinds of viral replicase/RdRP with more compact and less structural RdRP-BS motifs for overcoming the problems of the previous replicon-based saRNA/samRNA designs.

Logically, a real samRNA should be able to be amplified in RCR with its corresponding RdRP/replicase enzyme(s) thereof. Yet, all prior saRNA/samRNA designs and methods using either alphaviral CSE or SARS-CoV-1 5'/3'-UTR RdRP-binding regions fail to prove or achieve this key point due to lack of any useful RdRP-binding site motifs required for RCR-amplifiable template preparation. In view of the problems of prior saRNA/samRNA designs, it is herein highly desirable to develop a novel samRNA composition not only with more defined (compact) and less structural replicase/RdRP-binding sites but also without the necessity of any replicon-based construct for its amplification, so as to really achieve in-vitro samRNA production and amplification using the presently invented RCR methodology.

SUMMARY OF THE INVENTION

The principle of the present invention is relied on the incorporation of at least a specific coronaviral (e.g. COVID-19-associated viruses) and/or hepatitis C viral (HCV) replicase/RdRP-binding (recognition) site into the 5'-end or 3'-end region, or both, of a desired RNA/mRNA sequence, so as to form a self-amplifying RNA/mRNA (samRNA) platform template that can be amplified by using replicase/RdRP-mediated cycling reaction (RCR; U.S. patent application Ser. No. 17/648,336 and Ser. No. 17/648,340 to Lin). Using RCR, the amplified samRNA products can be further served as new templates for generating either the sense (+) or antisense (−) strands, or both, of the desired RNA/mRNA sequences. Since the present invention adopts specifically defined replicase/RdRP-binding site (RdRP-BS) motifs, but not any viral genome-derived replicon/plasmid, all prior replicon-based self-replicating RNA (saRNA) designs are obviously not compatible with current RCR methods and hence not comparable to the present invention. For instance, those prior replicon/plasmid-based saRNA designs and methods inlcude U.S. Pat. No. 11,291,635 to Geall et al. and U.S. Pat. Nos. 11,504,421 and 11,510,973 to Blair et al.

In RCR, the identified replicase/RdRP-binding sites (RdRP-BS) are served as a promoter-like and/or enhancer-like motif or motif combination for initiating replicase/RdRP activities in vitro. As shown in FIG. 2, after incorporation of at least an RdRP-BS motif into the 5'- and/or 3'-end region, or both, of a desired RNA/mRNA sequence (so as to form a samRNA template), the numbers of RdRP-BS-incorporated RNA/mRNA sequences can be amplified over 3~15 to 100~1000 folds, depending on the binding efficiency of the used RdRP-BS to its corresponding replicase/RdRP enzymes, in each cycle of RCR. Mechanistically, the sense-strand (+) RNA sequences of the samRNA template are first used to synthesize the antisense-strand (−) RNA sequences, while the resulting antisense-strand (−) RNA sequences are then served as reverse templates for amplifying the sense-strand (+) RNAs, and so on. Hence, both of the sense-strand (+) and antisense-strand (−) RNAs can be mutually used as templates for amplifying the desired RNA/mRNA sequences in RCR. As a result, all the resulting sense-strand (+) and antisense-strand (−) RNA products so obtained in RCR are self-amplifying RNAs/mRNAs (samRNAs). Based on this proof-of-concept principle of the present invention, it is conceivable that the same RCR principle may be adopted to use other different viral replicases/RdRP enzymes and their corresponding RdRP-BS motifs for designing and producing various samRNA constructs.

A samRNA platform may contain either 5'-end or 3'-end RdRP-BS, or most preferably both (FIG. 3). For structural clarification, the 5'-end RdRP-BS of the sense-strand (+) samRNA is complementary to the 3'-end RdRP-BS of the antisense-strand (−) samRNA, while the 3'-end RdRP-BS of the sense-strand (+) samRNA is complementary to the 5'-end RdRP-BS of the antisense-strand (−) samRNA. Yet, in a samRNA strand sequence, the 5'-end and 3'-end RdRP-BS may or may not share homology or complementarity to each other. In this regard, it is not necessary to contain any homology or complementarity between the 5'-end and 3'-end RdRP-BS of the same samRNA strand.

Each cycle of RCR can provide an amplification rate of about 3~15 to over 100~1000 folds in a 20 min-2 hour time period, depending on not only the length and structural complexity of the samRNA construct but also the combination and affinity strength of the used RdRP-BS motifs. In details, different RdRP-BS motifs, or the combination thereof, can provide different binding efficiency to the corresponding replicase/RdRP enzymes, leading to different RNA amplification rates. Hence, using different strong and/or weak RdRP-BS motifs, or the combination thereof, in the different ends of a samRNA sequence, we can selectively amplify either the sense-strand (+) or antisense-strand (−), or both, of samRNA with a relatively high purity ratio (maximally about 14/15 to >999/1000 purity, depending on the different amplification rates of 5'-end versus 3'-end RdRP-BS motifs). Also, the desired samRNA templates and the resulting samRNA products in RCR can be more than one kind and the starting and resulting samRNA sequences can be in either single-stranded or double-stranded conformation, or both.

To prepare RCR-amplifiable (or called RCR-ready) samRNA platform templates (FIG. 2), we preferably use reverse transcription (RT) and/or polymerase chain reaction (PCR) to incorporate at least a coronaviral (e.g. COVID-19 SARS-CoV-2) and/or HCV replicase/RdRP-binding site (RdRP-BS) into the 5'-end or 3'-end region, or both, of the complementary DNA (cDNA) of a desired RNA/mRNA sequence. Practically, at least a RdRP-BS is synthetically incorporated into the sequences of RT and/or PCR primers (called RCR-ready primers). After PCR or RT-PCR, the resulting cDNA products (namely RCR-ready cDNA templates) of the desired samRNA platform(s) are formed. For long-term preservation, the resulting RCR-ready cDNA templates can be further cloned into a plasmid or viral vector. Using these RCR-ready cDNA templates, an IVT reaction is performed to generate the first strands of the desired samRNA platform sequences. After further purification to remove the cDNA contents, the resulting samRNA platform sequences can then be used as starting templates in RCR to repeatedly produce and amplify the desired RNA/mRNA (samRNA) sequences. Alternatively, since IVT and RCR can be performed simultaneously under the same buffered conditions, the RCR-ready cDNA templates can also be used as a starting material for producing and amplifying the desired samRNA sequences in a combined IVT-RCR reaction.

Based on our previous studies of various coronaviral (e.g. COVID-19-associated virus strains) and HCV genomes, we had not only identified but also further modified several conserved homolog motifs of replicase/RdRP-binding sites (RdRP-BS), including 5'-end and 3'-end RdRP-BS, respectively (FIG. 3). As shown in the claimed priority invention U.S. patent application Ser. No. 17/648,336 and Ser. No. 17/648,340, these identified RdRP-BS motifs may share high homology and/or complementarity to each other. In details, the 5'-end RdRP-BS contains at least a consensus sequence homologous to either 5'-AU(G/C)(U/−)G(A/U)-3' (e.g. 5'-AUSUGW-3'; SEQ ID NO:1) or 5'-U(C/−)(U/A)C (U/C)(U/A)A-3' (e.g. 5'-UCWCYWA-3'; SEQ ID NO:2), or both, while the 3'-end RdRP-BS contains at least a consensus sequence homologous to either 5'-(U/A)C(A/−)(C/G) AU-3' (e.g. 5'-WCASAU-3'; SEQ ID NO:3) or 5'-U(A/U) (A/G)G(A/U)(G/−) A-3' (e.g. 5'-UWRGWR-3'; SEQ ID NO:4), or both. Preferably, the 5'-end RdRP-BS may contain at least a sequence homologous to 5'-AUCUGU-3' (SEQ ID NO:5), 5'-UCUCUAA-3' (SEQ ID NO:6), 5'-UCUCCUA-3' (SEQ ID NO:7), and/or 5'-UUCAA-3' (SEQ ID NO:8), or a combination thereof, while the 3'-end RdRP-BS may contain at least a sequence homologous to 5'-ACAGAU-3' (SEQ ID NO:9), 5'-UUAGAGA-3' (SEQ ID NO:10), 5'-UAGGAGA-3' (SEQ ID NO:11), and/or 5'-UUGAA-3' (SEQ ID NO:12), or a combination thereof. Also, the 5'-end and 3'-end RdRP-BS can be used together with each other to form different combinations with different binding efficiency in order to selectively amplify one strand RNA over the other strand. For example, SEQ ID NO:8 and SEQ ID NO:12 are often used combinedly with other RdRP-BS motifs for further enhancing or reducing replicase/RdRP binding efficiency. Notably, in all these identified RdRP-BS motifs, the contents of uridine/uracil (U) and thymidine/thymine (T) are exchangeable. Also, the uridine/uracil (U) contents of the desired samRNA sequences may be completely or partially replaced by pseudouridine, methyluridine, methoxyuridine, and/or other related or similarly modified nucleotide analogs, or a combination thereof. Furthermore, for preventing RNA degradation, the 3'-end of the samRNA platform templates as well as the resulting samRNA products may be further tailed by at least a 3'-cap-like molecule, such as 5'-phosphorothioate-uridine (PU), 5'-phosphoadenosine 3'-phosphate (PAP), and/or adenosine 3'-phosphate 5'-phosphosulfate (PAPS).

In order to further improve RCR efficiency, the present invention herein demonstrates an optimized 5'/3'-RdRP-BS combination (FIG. 7), using the previously identified 5'-end and 3'-end RdRP-BS sequences, including homologs of SEQ ID NO:1, SEQ ID NO:2, SEQ ID NO:3, and/or SEQ ID NO:4. In details, the improved 5'-end RdRP-BS contains homologs of at least a 5'-GAYYTSTTYY CTAR-3' (SEQ ID NO:13) and at least a 5'-RTAGYYAASA YYTC-3' (SEQ ID NO:14) sequence, wherein SEQ ID NO:13 and SEQ ID NO:14 are separated by a three (3)-twenty (20)-nucleotide (nt) linker sequence which is neither homologous nor complementary to the SEQ ID NO:13 and SEQ ID NO:14. On the other hand, the improved 3'-end RdRP-BS contains homologs of at least a 5'-GTRRCSTTRR CTAY-3' (SEQ ID NO:15) and at least a 5'-YTAGRRAASG RRAC-3' (SEQ ID NO:16) sequence, wherein SEQ ID NO:15 and SEQ ID NO:16 are separated by another 3~20-nt linker sequence which is neither homologous nor complementary to the SEQ ID NO:15 and SEQ ID NO:16. The positions of these improved 5'- and 3'-end RdRP-BS in the samRNA are mutually exchangeable. Also, in the SEQ ID NOs:13-16, Y and R are exchangeable. Notably, both of the linker sequences may be the same or different. Also, the linker sequence may or may not form a hairpin-like stem-loop structure within its own sequences, but not to the other linker sequence. By definition, the nucleotide abbreviation of Y is C or T (U), S is G or C, and R is A or G. As shown in FIG. 3, an optimized samRNA platform construct is formed by adding the improved 5'-end RdRP-BS in the 5'-end region and the improved 3'-end RdRP-BS in the 3'-end region of a desired RNA/mRNA sequence, respectively. Moreover, the desired RNA/mRNA sequence may further contain at least a kozak motif, internal ribosome entry site (IRES), poly-A signal, and/or poly-A tail, or a combination thereof.

The optimized samRNA platform sequences may further comprise a 5'-end cap (5'-cap) molecule, such as m7G(5')ppp(5')N(m7G; cap-0) and/or its related cap-1/cap-2 analogs, wherein said 5'-cap molecule is incorporated into the optimized samRNA preferably using the subunits or accessory proteins of isolated, recombinant or modified coronaviral RdRP enzymes, including but not limited to NSP12, NSP9, NSP14, and/or NSP10/16 proteins, or a combination thereof. Also, the samRNA so obtained may further comprise at least a kozak motif sequence for facilitating protein/peptide translation in mammalian cells. Due to our recent testing and further modification of the identified RdRP-BS motifs, the currently available coronaviral (e.g. COVID-19 SARS-CoV-2) and HCV RdRP enzymes as well as the associated accessory proteins can be used to produce and amplify either 5'-capped sense (+) or antisense (−) strands, or both, of the desired samRNA sequences in vitro, ex vivo as well as in vivo.

Since the full integrity of both 5'-end and 3'-end RdRP-BS are required for maintaining the cycling reaction of RCR, all of the amplified samRNA products must carry intact 5'- and 3'-end RdRP-BS and thus are all preserved well in their full-length conformation. Notably, the 5'-end and 3'-end RdRP-BS of a samRNA sequence may be the same or different from each other. Also, the samRNA platform and its resulting samRNA products may contain single or multiple 5'-end and/or 3'-end RdRP-BS motifs, respectively. Moreover, the 5'- and 3'-end RdRP-BS of a samRNA sequence may or may not be complementary to each other and their complementarity can be partially or perfectly matched to each other. Noteworthy, the combination of multiple 5'- and/or 3'-end RdRP-BS motifs can further enhance the efficiency of RCR-based samRNA amplification. With intact 5'- and 3'-end RdRP-BS, the resulting samRNA products, including both sense (+) and antisense (−) strand samRNAs, can be further used as templates in RCR for samRNA amplification. Alternatively, they may also form double-stranded RNAs (dsRNA). Hence, the starting samRNA templates of RCR can be either single- or double-stranded RNAs, or a combination thereof.

In one preferred embodiment, the desired samRNA sequence (i.e, containing mRNA or microRNA, or any other kind of RNA species) is flanked with at least an RdRP-BS in both of its 5'- and 3'-end regions. Since both ends of the desired samRNA carry at least an RdRP-BS for eliciting replicase/RdRP activities, both of the sense-strand (+) and antisense-strand (−) samRNA are used as starting templates for amplifying each other simultaneously, so as to form a complete RCR cycle for maximal samRNA amplification. The resulting samRNA so obtained can be in either single-stranded or double-stranded conformation, depending on the binding efficiency and respective amplification rate of 5'-end versus 3'-end RdRP-BS to the corresponding RdRP. Also, the sense-strand (+) and antisense-strand (−) samRNA sequences may further form double-stranded RNAs (dsRNA), facilitating the further processing of dsRNA into siRNAs, shRNAs, miRNAs, and/or piRNA constructs of interest.

Alternatively, in another preferred embodiment, the desired samRNA sequence contains at least a strong RdRP-BS in its either 5'-end or 3'-end region, while containing another weak or none RdRP-BS in the other end. In this way, we can selectively amplify either the sense (+) or antisense (−) strands of the samRNA, leading to preferential amplification of one specific strand of the samRNA. This approach is useful for generating and amplifying either the mRNA or antisense RNA (aRNA, ASO) of a specific functional protein, viral antigen and/or antibody, facilitating the design and development of mRNA vaccines, RNA medicines and/or antibody-based medicines. Notably, the resulting mRNA vaccines and RNA/antibody-based medicines so obtained are pharmaceutical compositions useful for treating a variety of human diseases, including but not limited to Alzheimer's disease, Parkinson's disease, motor neuron disease, stroke, diabetes, myocardial infraction, hemophilia, anemia, leukemia, and all sorts of cancers as well as all kinds of viral and bacterial infections.

Conceivably, our new RCR methodology can be used to produce and amplify a variety of RNA species carrying at least an RdRP-BS, particularly viral antigen mRNAs and/or known functional mRNAs as well as non-coding RNAs, all of which are useful for designing and developing anti-viral vaccines and/or anti-disease medicines, and likely many more potential applications. For example, as shown in our priority U.S. patent application Ser. No. 17/489,357 and Ser. No. 17/648,336, we had developed various new samRNA designs and applications for generating novel RNA vaccines and medicines for treating infectious diseases and cancers. Also, by co-transfection of a designed microRNA-coding samRNA and another isolated RdRP mRNA/samRNA into human somatic cells, our priority U.S. patent application Ser. No. 17/648,340 had demonstrated another novel method for inducing iPS cell generation in vitro as well as in vivo. Moreover, the samRNA so obtained can be used in an in-vitro, in-cell and/or in-vivo translation system for producing the encoded proteins, peptides and/or antibodies of interest. In view of these prior proof-of-principle designs and utilizations, the development of many more potential applications of the present invention is highly expected.

For producing highly structured samRNA templates, our priority U.S. patent application Ser. No. 17/489,357 had developed a novel PCR-IVT method for overcoming the low efficiency problem of highly structured RNA/mRNA generation in vitro. Because the presence of hairpin- and/or stem-loop-like RNA structures greatly hinders RNA transcription in vitro, even a skilled person in the art can not expect the efficiency of highly structured RNA/mRNA generation using IVT. In fact, a hairpin-like or stem-loop structure may resemble an intrinsic transcription termination signal for prokaryotic RNA polymerases (McDowell et al, *Science* 266:822-825, 1994). To solve this problem, our priority method adopts a new IVT system with a mixture activity of RNA polymerases and special helicases. The additional helicase activity used in IVT (and in RCR as well) markedly reduces the secondary structures of both DNA/RNA templates and their resulting RNA/mRNA products for more efficiently producing highly structured RNAs/mRNAs. Accordingly, an improved buffer system is also invented to enhance the efficiency of the mixed RNA polymerase and helicase activity in IVT (and RCR as well in our recent studies). Interestingly, although several prior studies had reported that helicase may be involved in prokaryotic transcription termination, our studies however demonstrate a new functionality of coronaviral helicases for enhancing RNA/mRNA amplification in IVT (and in IVT-RCR as well). Based on our recent studies, coronaviral NSP7 and NSP13 proteins are two of the identified helicases useful for enhancing RNA/mRNA amplification efficiency of IVT and IVT-RCR.

For facilitating intracellular delivery/transfection under various in-vitro, ex-vivo and/or in-vivo conditions, the samRNA and another RdRP mRNA/samRNA may be together or separately mixed, conjugated, encapsulated or formulated with at least a delivery/transfection agent selected from, but not limited to, liposomes, nanoparticles, liposomal nanoparticles (LNP), exosomes, sugar-/glucosamine-/galatosamine-based conjugating molecules, infusion/transfusion agents, glycylglycerin-derived agents, gene gun materials, electroporation agents, and/or transposons/retrotransposons, or a combination thereof.

The advantages of RCR-amplifiable samRNA compositions include (1) high RNA yield rate, (2) high full-length integrity, (3) high RNA purity, (4) long-lasting efficacy, (5) relatively small size for easy intracellular transfection, (6)

simple and inexpensive production procedure, (7) simple equipment requirement, and (8) versatile applications developed. Conceivably, the RCR-amplifiable samRNA compositions of the present invention are extremely useful for designing and developing all sorts of RNA/mRNA medicines as well as vaccines for treating a variety of human diseases, including but not limited to Alzheimer's disease, Parkinson's disease, motor neuron disease, stroke, diabetes, myocardial infraction, hemophilia, anemia, leukemia, and many kinds of cancers as well as all sorts of viral and bacterial infections. Due to this technology breakthrough, a whole new line of nucleic acid medicines can be further designed and developed based on the RCR method and its related samRNA compositions of the present invention.

A. Definitions

To facilitate understanding of the invention, a number of terms are defined below:

Nucleic Acid: a polymer of deoxyribonucleic acid (DNA) or ribonucleic acid (RNA), either single or double stranded.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. A nucleoside containing at least one phosphate group bonded to the 3' or 5' position of the pentose is a nucleotide. DNA and RNA are consisted of different types of nucleotide units called deoxyribonucleotide and ribonucleotide, respectively.

Deoxyribonucleoside Triphosphates (dNTPs): the building block molecules for DNA synthesis, including dATP, dGTP, dCTP, and dTTP and sometimes may further containing some modified deoxyribonucleotide analogs.

Ribonucleoside Triphosphates (rNTPs): the building block molecules for RNA synthesis, including ATP, GTP, CTP, and UTP and sometimes may further containing pseudouridine, 5' methyluridine, methoxyuridine, and/or some other modified ribonucleotide analogs.

Nucleotide Analog: a purine or pyrimidine nucleotide that differs structurally from adenine (A), thymine (T), guanine (G), cytosine (C), or uracil (U), but is sufficiently similar to substitute for the normal nucleotide in a nucleic acid molecule.

Oligonucleotide: a molecule comprised of two or more monomeric units of DNA and/or RNA, preferably more than three, and usually more than ten. An oligonucleotide longer than 13 nucleotide monomers is also called polynucleotiude. The exact size will depend on many factors, which in turn depends on the ultimate function or use of the oligonucleotide. The oligonucleotide may be generated in any manner, including chemical synthesis, DNA replication, RNA transcription, reverse transcription, or a combination thereof.

Nucleic Acid Composition: a nucleic acid composition refers to an oligonucleotide or polynucleotide such as a DNA or RNA sequence, or a mixed DNA/RNA sequence, in either a single-stranded or a double-stranded molecular structure.

Gene: a nucleic acid composition whose oligonucleotide or polynucleotide sequence codes for an RNA and/or a polypeptide (protein). A gene can be either RNA or DNA. A gene may encode a non-coding RNA, such as small hairpin RNA (shRNA), microRNA (miRNA), rRNA, tRNA, snoRNA, snRNA, and their RNA precursors as well as derivatives. Alternatively, a gene may encode a protein-coding RNA essential for protein/peptide synthesis, such as messenger RNA (mRNA) and its RNA precursors as well as derivatives. In some cases, a gene may encode a protein-coding RNA that also contains at least a microRNA or shRNA sequence.

Primary RNA Transcript: an RNA sequence that is directly transcribed from a gene without any RNA processing or modification.

Precursor messenger RNA (pre-mRNA): primary RNA transcripts of a protein-coding gene, which are produced by eukaryotic type-II RNA polymerase (Pol-II) machineries in eukaryotes through an intracellular mechanism termed transcription. A pre-mRNA sequence contains a 5'-untranslated region (UTR), a 3'-UTR, exons and introns.

Intron: a part or parts of a gene transcript sequence encoding non-protein-reading frames, such as in-frame intron, 5'-UTR and 3'-UTR.

Exon: a part or parts of a gene transcript sequence encoding protein-reading frames (cDNA), such as cDNA for cellular genes, growth factors, insulin, antibodies and their analogs/homologs as well as derivatives.

Messenger RNA (mRNA): assembly of pre-mRNA exons, which is formed after intron removal by intracellular RNA splicing machineries (e.g. spliceosomes) and served as a protein-coding RNA for peptide/protein synthesis. Structurally, mRNA sequence may comprise 5'-cap nucleotide [e.g. m7G(5')ppp(5')N-] (m7G), 5'-untranslated region (5'-UTR), at least a Kozak consensus translation initiation site (e.g. 5'-GCCACC-3'), at least a protein/peptide-coding region, polyadenylation (poly-A) signals (e.g. 5'-AUAAA-3' or 5'-AUUAAA-3'), and/or 3'-UTR with or without a poly-A tail. The proteins/peptides encoded by mRNAs include, but not limited to, enzymes, growth factors, insulin, antibodies and their analogs/homologs as well as derivatives.

Complementary DNA (cDNA): a single-stranded or double-stranded DNA that contains a sequence complementary to an mRNA sequence and does not contain any intronic sequence.

Sense: a nucleic acid molecule in the same sequence order and composition as the homologous mRNA. The sense conformation is indicated with a "+", "s" or "sense" symbol.

Antisense: a nucleic acid molecule complementary to the respective mRNA molecule. The antisense conformation is indicated as a "—" symbol or with an "a" or "antisense" in front of the DNA or RNA, e.g., "cDNA" or "aRNA".

Base Pair (bp): a partnership of adenine (A) with thymine (T), or of cytosine (C) with guanine (G) in a double stranded DNA molecule. In RNA, uracil (U) is substituted for thymine. Generally the partnership is achieved through hydrogen bonding. For example, a sense nucleotide sequence "5'-A-T-C-G-U-3'" can form complete base pairing with its antisense sequence "5'-A-C-G-A-T-3'".

5'-end: a terminus lacking a nucleotide at the 5' position of successive nucleotides in which the 5'-hydroxyl group of one nucleotide is joined to the 3'-hydroyl group of the next nucleotide by a phosphodiester linkage. Other groups, such as one or more phosphates, may be present on the terminus.

3'-end: a terminus lacking a nucleotide at the 3' position of successive nucleotides in which the 5'-hydroxyl group of one nucleotide is joined to the 3'-hydroyl group of the next nucleotide by a phosphodiester linkage. Other groups, most often a hydroxyl group, may be present on the terminus.

Template: a nucleic acid molecule being copied by a nucleic acid polymerase. A template can be single-stranded, double-stranded or partially double-stranded, RNA or DNA, depending on the polymerase. The synthesized copy is complementary to the template, or to at least one strand of a double-stranded or partially double-stranded template. Both RNA and DNA are synthesized in the 5' to 3' direction.

The two strands of a nucleic acid duplex are always aligned so that the 5' ends of the two strands are at opposite ends of the duplex (and, by necessity, so then are the 3' ends).

Nucleic Acid Template: a double-stranded DNA molecule, double-stranded RNA molecule, hybrid molecules such as DNA-RNA or RNA-DNA hybrid, or single-stranded DNA or RNA molecule.

Conserved: a nucleotide sequence is conserved with respect to a pre-selected (referenced) sequence if it non-randomly hybridizes to an exact complement of the pre-selected sequence.

Homologous or Homology: a term indicating the similarity between a polynucleotide and a gene or mRNA sequence. A nucleic acid sequence may be partially or completely homologous to a particular gene or mRNA sequence, for example. Homology may be expressed as a percentage determined by the number of similar nucleotides over the total number of nucleotides.

Complementary or Complementarity or Complementation: a term used in reference to matched base pairing between two polynucleotides (e.g. sequences of an mRNA and a cDNA) related by the aforementioned "base pair (bp)" rules. For example, the sequence "5'-A-G-T-3" is complementary to not only the sequence "5'-A-C-T-3" but also to "5'-A-C-U-3". Complementation can be between two DNA strands, a DNA and an RNA strand, or between two RNA strands. Complementarity may be "partial" or "complete" or "total". Partial complementarity or complementation occurs when only some of the nucleic acid bases are matched according to the base pairing rules. Complete or total complementarity or complementation occurs when the bases are completely or perfectly matched between the nucleic acid strands. The degree of complementarity between nucleic acid strands has significant effects on the efficiency and strength of hybridization between nucleic acid strands. This is of particular importance in amplification reactions, as well as in detection methods that depend on binding between nucleic acids. Percent complementarity or complementation refers to the number of mismatch bases over the total bases in one strand of the nucleic acid. Thus, a 50% complementation means that half of the bases were mismatched and half were matched. Two strands of nucleic acid can be complementary even though the two strands differ in the number of bases. In this situation, the complementation occurs between the portion of the longer strand corresponding to the bases on that strand that pair with the bases on the shorter strand.

Complementary Bases: nucleotides that normally pair up when DNA or RNA adopts a double stranded configuration.

Complementary Nucleotide Sequence: a sequence of nucleotides in a single-stranded molecule of DNA or RNA that is sufficiently complementary to that on another single strand to specifically hybridize between the two strands with consequent hydrogen bonding.

Hybridize and Hybridization: the formation of duplexes between nucleotide sequences which are sufficiently complementary to form complexes via base pairing. Where a primer (or splice template) "hybridizes" with target (template), such complexes (or hybrids) are sufficiently stable to serve the priming function required by a DNA polymerase to initiate DNA synthesis. There is a specific, i.e. non-random, interaction between two complementary polynucleotides that can be competitively inhibited.

Posttranscriptional Gene Silencing: a targeted gene knockout or knockdown effect at the level of mRNA degradation or translational suppression, which is usually triggered by either foreign/viral DNA or RNA transgenes or small inhibitory RNAs.

RNA Interference (RNAi): a posttranscriptional gene silencing mechanism in eukaryotes, which can be triggered by small inhibitory RNA molecules such as microRNA (miRNA), small hairpin RNA (shRNA) and small interfering RNA (siRNA). These small RNA molecules usually function as gene silencers, interfering with expression of intracellular genes containing either completely or partially complementarity to the small RNAs.

MicroRNA (miRNA): single-stranded RNAs capable of binding to targeted gene transcripts that have partial complementarity to the miRNA. MiRNA is usually about 17-27 oligonucleotides in length and is able to either directly degrade its intracellular mRNA target(s) or suppress the protein translation of its targeted mRNA, depending on the complementarity between the miRNA and its target mRNA. Natural miRNAs are found in almost all eukaryotes, functioning as a defense against viral infections and allowing regulation of gene expression during development of plants and animals.

Precursor MicroRNA (Pre-miRNA): hairpin-like single-stranded RNAs containing stem-arm and stem-loop regions for interacting with intracellular RNaseIII endoribonucleases to produce one or multiple microRNAs (miRNAs) capable of silencing a targeted gene or genes complementary to the microRNA sequence(s). The stem-arm of a pre-miRNA can form either a perfectly (100%) or a partially (mis-matched) hybrid duplexes, while the stem-loop connects one end of the stem-arm duplex to form a circle or hairpin-loop conformation. In the present invention, however, precursor of microRNA may also includes pri-miRNA.

Small interfering RNA (siRNA): short double-stranded RNAs sized about 18-27 perfectly base-paired ribonucleotide duplexes and capable of degrading target gene transcripts with almost perfect complementarity.

Small or short hairpin RNA (shRNA): single-stranded RNAs that contain a pair of partially or completely matched stem-arm nucleotide sequences divided by an unmatched loop or bubble oligonucleotide to form a hairpin-like structure. Many natural miRNAs are derived from small hairpin-like RNA precursors, namely precursor microRNA (pre-miRNA).

Vector: a recombinant nucleic acid composition such as recombinant DNA (rDNA) capable of movement and residence in different genetic environments. Generally, another nucleic acid is operatively linked therein. The vector can be capable of autonomous replication in a cell in which case the vector and the attached segment is replicated. One type of preferred vector is an episome, i.e., a nucleic acid molecule capable of extrachromosomal replication. Preferred vectors are those capable of autonomous replication and expression of nucleic acids. Vectors capable of directing the expression of genes encoding for one or more polypeptides and/or non-coding RNAs are referred to herein as "expression vectors" or "expression-competent vectors". Particularly important vectors allow cloning of cDNA from mRNAs produced using a reverse transcriptase. A vector may contain components consisting of a viral or a type-II RNA polymerase (Pol-II or poi-2) promoter, or both, a Kozak consensus translation initiation site (such as 5'-GCCRCC-3'), polyadenylation signals (such as 5'-AUAAA-3' or 5'-AUUAAA-3'), a plurality of restriction/cloning sites, a pUC origin of replication, a SV40 early promoter for expressing at least an antibiotic resistance gene in replication-competent prokaryotic cells, an optional SV40 origin for replication in mammalian cells, and/or a tetracycline responsive element. The structure of a vector can be a linear or circular form of single- or double-stranded DNA selected form the group consisting of plasmid, viral vector, transposon, retrotransposon, DNA transgene, jumping gene, and a combination thereof.

Promoter: a nucleic acid to which a polymerase molecule recognizes, perhaps binds to, and initiates RNA transcription. For the purposes of the instant invention, a promoter can be a known polymerase binding site, an enhancer and the like, any sequence that can initiate synthesis of RNA transcripts by a desired polymerase.

RNA Processing: a cellular mechanism responsible for RNA maturation, modification and degradation, including RNA splicing, intron excision, exosome digestion, nonsense-mediated decay (NMD), RNA editing, RNA processing, 5'-capping, 3'-poly(A) tailing, and a combination thereof.

Gene Delivery: a genetic engineering method selected from the group consisting of polysomal transfection, liposomal transfection, chemical (nanoparticle) transfection, electroporation, viral infection, DNA recombination, transposon insertion, jumping gene insertion, microinjection, gene-gun penetration, and a combination thereof.

Genetic Engineering: a DNA recombination method selected from the group consisting of DNA restriction and ligation, homologous recombination, transgene incorporation, transposon insertion, jumping gene integration, retroviral infection, and a combination thereof.

Transfected Cell: a single or a plurality of eukaryotic cells after being artificially inserted with at least a nucleic acid sequence or protein/peptide molecule into the cell(s), selected from the group consisting of a somatic cell, a tissue cell, a stem cell, a germ-line cell, a tumor cell, a cancer cell, a virus-infected cell, and a combination thereof.

Antibody: a peptide or protein molecule having a pre-selected conserved domain structure coding for a receptor capable of binding a pre-selected ligand.

Pharmaceutical and/or therapeutic Application: a biomedical utilization and/or apparatus useful for stem cell generation, drug/vaccine development, non-transgenic gene therapy, cancer therapy, disease treatment, wound healing, tissue/organ repair and regeneration, and high-yield production of proteins/peptides/antibodies, drug ingredients, medicines, vaccines and/or food supplies, and a combination thereof.

B. Compositions and Applications

A novel composition of self-amplifying RNA (samRNA), comprising:

At least a desired RNA sequence flanked with at lease a 5'-end RdRP-binding site and at least a 3'-end RdRP-binding site; wherein said 5'-end RdRP-binding site contains at least a 5'-GAYYTSTTYY CTAR-3' (SEQ ID NO:13) and at least a 5'-RTAGYYAASA YYTC-3' (SEQ ID NO:14) sequence and the SEQ ID NO:13 and SEQ ID NO:14 are separated by a 3~20-nucleotide linker sequence which is neither homologous nor complementary to the SEQ ID NO:13 and SEQ ID NO:14, while said 3'-end RdRP-binding site contains at least a 5'-GTRRCSTTRR CTAY-3' (SEQ ID NO:15) and at least a 5'-YTAGRRAASG RRAC-3' (SEQ ID NO:16) sequence and the SEQ ID NO:15 and SEQ ID NO:16 are separated by another 3~20-nucleotide linker sequence which is neither homologous nor complementary to the SEQ ID NO:15 and SEQ ID NO:16.

Notably, the positions of the improved 5'-end and 3'-end RdRP-binding sites in a samRNA are mutually exchangeable. Also, in the SEQ ID NOs:13~16, Y and R are exchangeable. By definition, the nucleotide abbreviation of Y is C or T (U), S is G or C, and R is A or G. Also, the contents of uridine/uracil (U) and thymidine/thymine (T) are mutually exchangeable. The desired RNA sequence may further contain at least a kozak motif, internal ribosome entry site (IRES), poly-A signal, and/or poly-A tail, or a combination thereof. Notably, the desired RNA sequence can be a mRNA that encodes protein/peptide and/or antibody or a non-coding RNA, such as siRNA, shRNA, and/or microRNA (miRNA)/pre-miRNA, or a combination thereof. Also, the desired RNA conformation can be either single stranded or double stranded, or a combination thereof. For increasing RNA stability, the uridine/uracil (U) contents of the desired RNA and its associated samRNA can be totally or partially replaced by pseudouridine, methyluridine, methoxyuridine, or other related/modified nucleotide analogs, or a combination thereof. Moreover, the samRNA and its derived samRNA products may further comprise a 5'-cap molecule, such as m7G (cap-0) and/or its related analogs (e.g. cap-1 or cap-2), which is preferably incorporated into the samRNA by using coronaviral NSP9/14 and/or NSP10/16, or a combination thereof. Furthermore, the 3'-end of the samRNA and its derived samRNA products may be further tailed by at least a 3'-cap molecule, including but not limited to 5'-phosphorothioate-uridine (PU), 5'-phosphoadenosine 3'-phosphate (PAP), and/or adenosine 3'-phosphate 5'-phosphosulfate (PAPS).

BRIEF DESCRIPTION OF THE DRAWINGS

Referring particularly to the drawings for the purpose of illustration only and not limitation, there is illustrated.

NSP12) in transfected human cells after co-transfection with RCR-ready miR-302 precursor microRNA samRNAs (samR-miR-302s) and coronaviral RdRP samRNA (as shown in most right), compared to the result of cells transfected with only the samR-miR-302s (in middle), demonstrating the evidence of RCR-based RNA amplification in the transfected cells.

Figure 5:
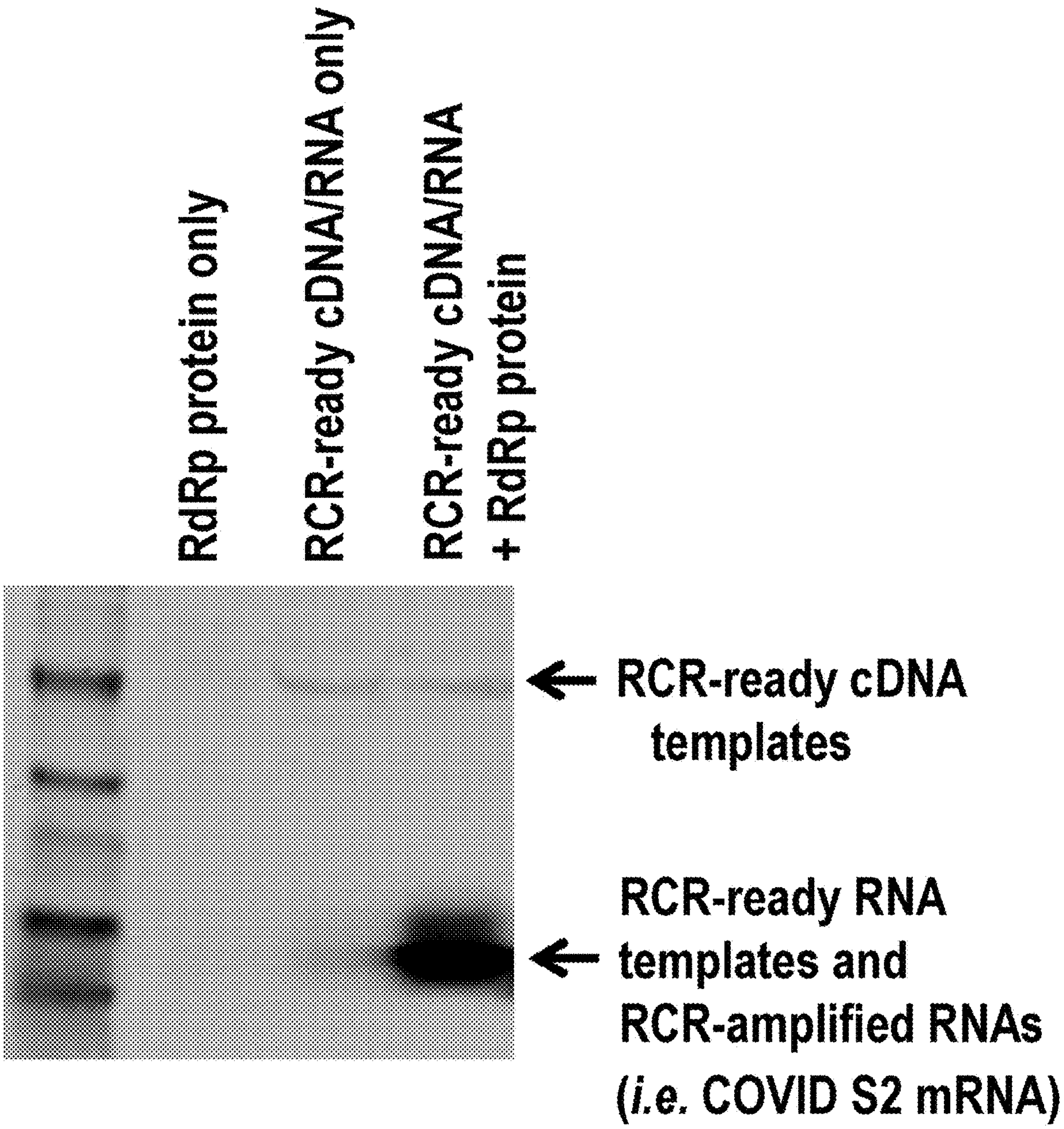

FIG. 5 shows Northern blot analysis results of RCR-ready cDNA and samRNA templates as well as the resulting samRNA products (e.g. samRNA sequences containing viral antigen proteins/peptides) amplified by coronaviral RdRP enzymes in an in-vitro IVT-RCR reaction in small test tubes, demonstrating the evidence of RCR in vitro.

Figure 1:
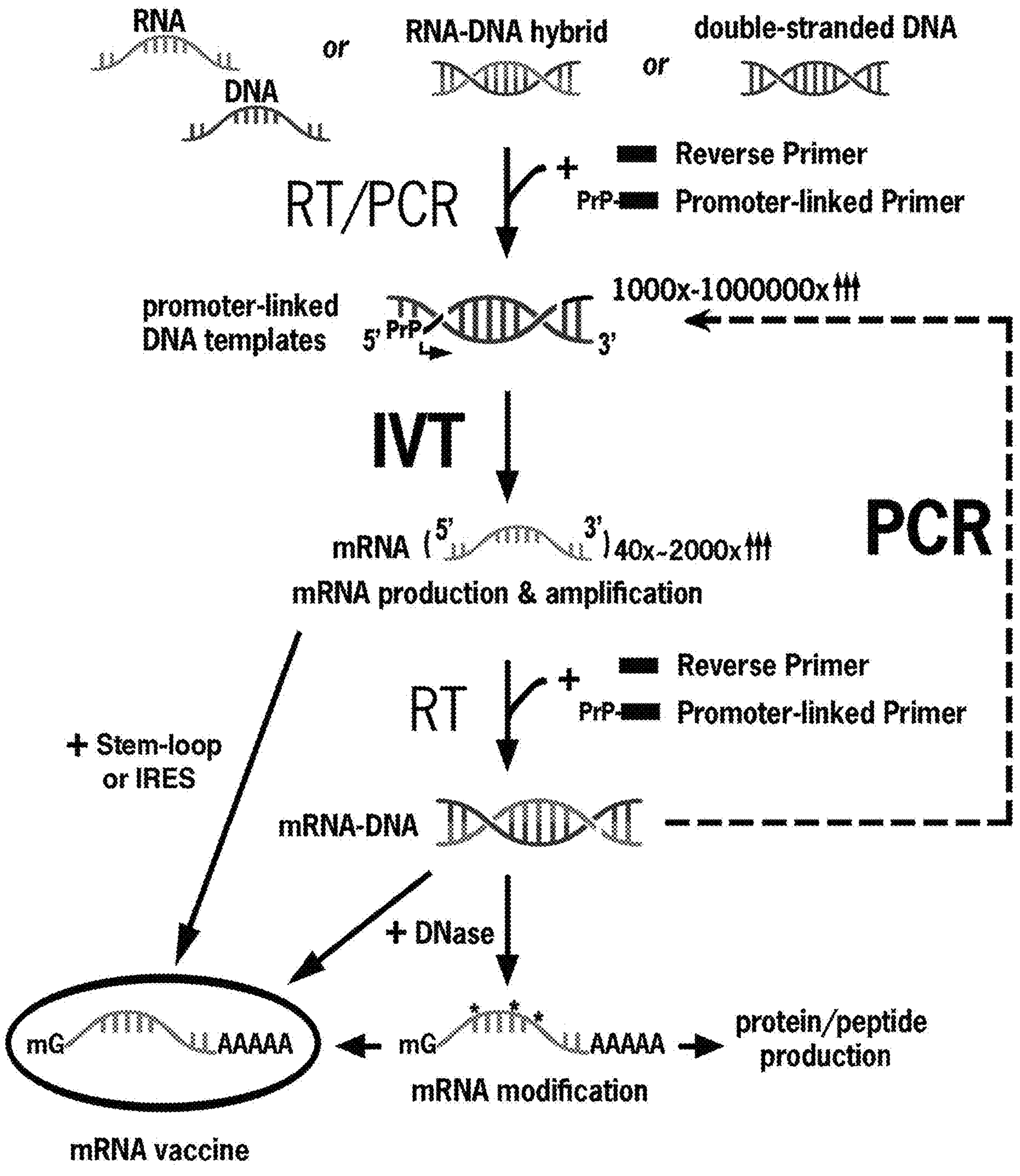
FIG. 1 depicts the step-by-step procedure of the prior PCR-IVT methodology. For RNA production, a part or whole procedure of this PCR-IVT protocol may be adopted for either single or multiple cycle amplification of a desired RNA/mRNA sequence.
Figure 2:
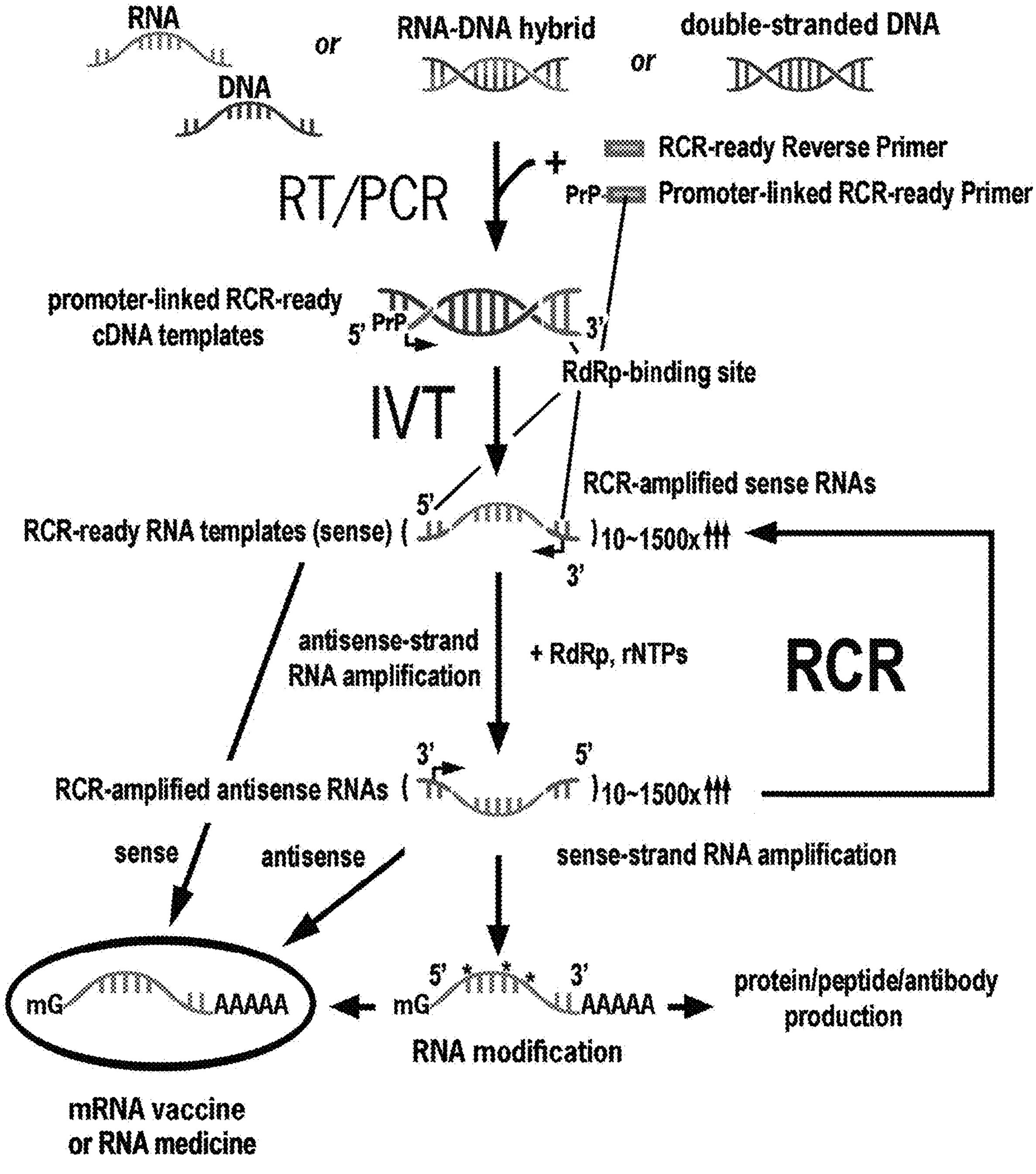
FIG. 2 depicts the step-by-step procedure of the presently invented RCR methodology. First, at least a coronaviral and/or HCV replicase/RdRP-binding site (RdRP-BS) is incorporated into the 5'-end or 3'-end, or preferably both, of the cDNAs of a desired RNA/mRNA sequence, using RT, PCR and/or PCR-IVT methods, so as to form RCR-ready cDNA/samRNA templates. After that, a part or whole procedure of this invented RCR method is used to produce and amplify the RdRP-BS-incorporated RNA/mRNA (or called samRNA) sequences from the RCR-ready cDNA/samRNA templates after single or multiple cycles of RCR. Alternatively, since IVT and RCR methods can be performed simultaneously under the same buffered condition, the RCR-ready cDNA/samRNA templates can also be used as starting materials for amplifying the desired RNA/mRNA sequences in a combined IVT-RCR reaction.
Figure 3:
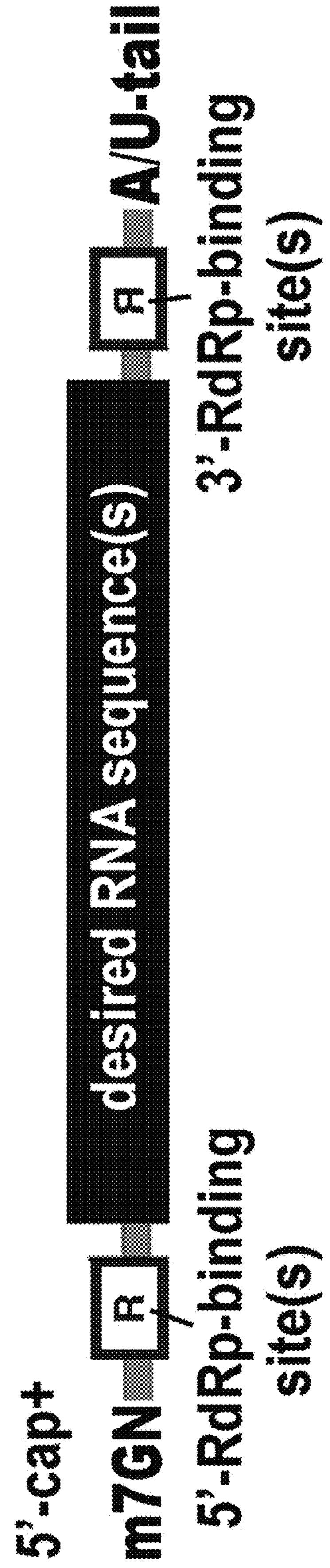
FIG. 3 depicts the structure of a designed RCR-ready samRNA platform template. It is noted that an RCR-ready cDNA template contains an extra 5'-end promoter sequence added to the double-stranded DNA version of this RCR-ready samRNA platform template. The RCR-ready cDNA template is used in IVT and IVT-RCR, while the RCR-ready samRNA platform template is used in RCR and IVT-RCR. For enhancing the stability of samRNA, all or part of the uridine/uracil (U) contents of the samRNA sequences can be replaced by pseudouridine, methyluridine, methoxyuridine, and/or other similar modified nucleotide analogs.
Figure 4:
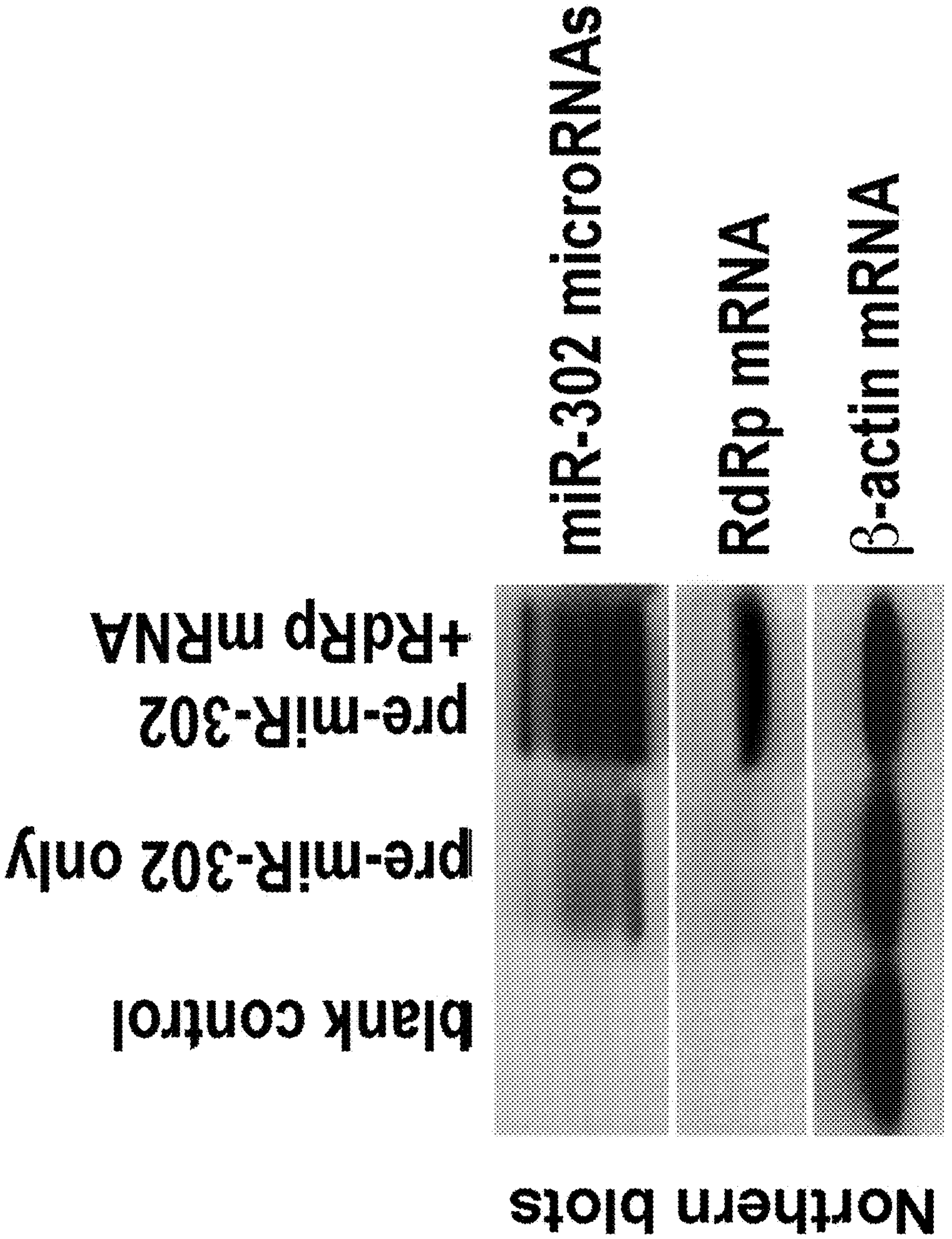
FIG. 4 shows the Northern blot analysis result of markedly increased expressions of miR-302 microRNAs (i.e. from top to bottom: b, c, d, a) and RdRP mRNA/samRNA (e.g. HCV NS5B or modified COVID-19 SARS-CoV-2
Figure 6:
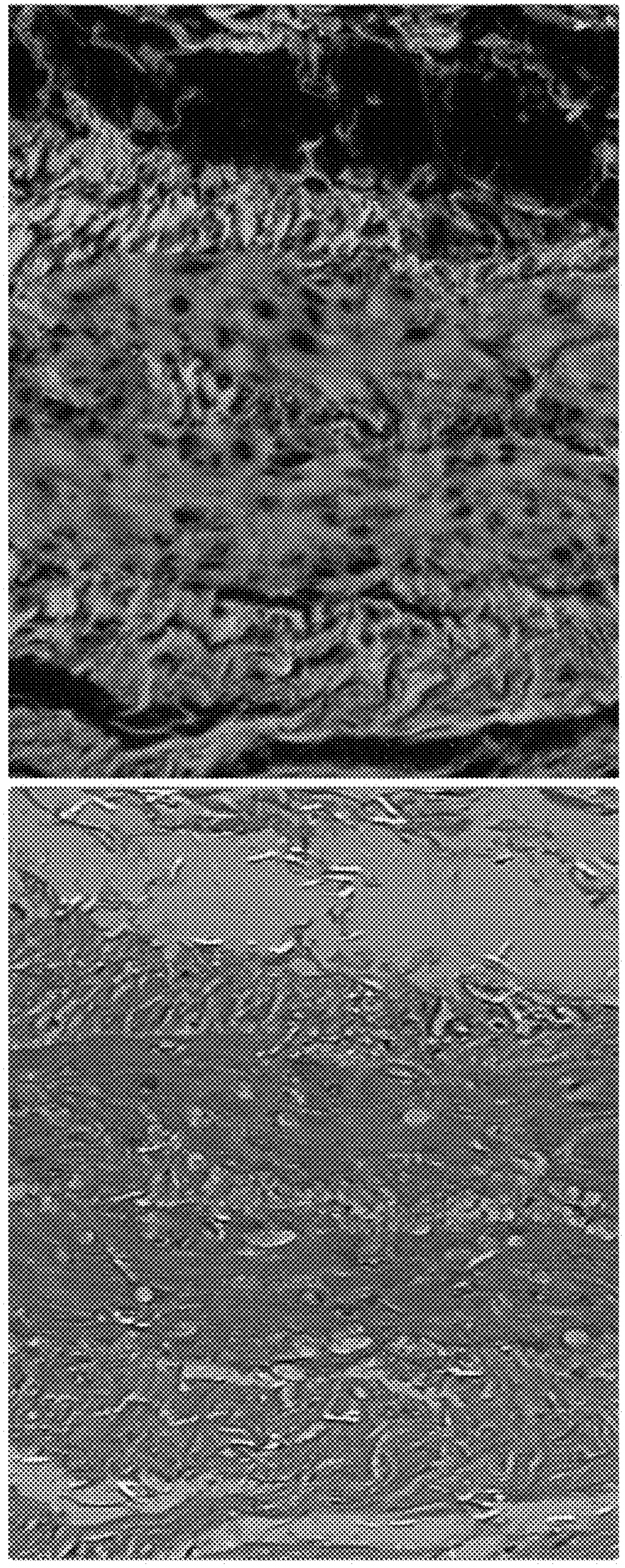

FIG. 6 shows the immunohistochemical (IHC) staining of coronaviral (e.g. COVID-19 SARS-CoV-2) spike S proteins (labeled with GFP-mAb) produced in the mouse muscle tissues in vivo after co-transfection with a mixture of RCR-amplified S protein samRNAs (from FIG. 5) and coronaviral RdRP samRNAs (from FIG. 4), indicating that the present invention is useful for developing and manufacturing anti-viral mRNA (samRNA) vaccines. Notably, our recent studies further show that the content of RdRP samRNAs may further contain transcripts of coronaviral NSP proteins, including but not limited to NSP12, NSP7, NSP9, NSP14, and/or NSP10/16, or a combination thereof.

Figure 7:
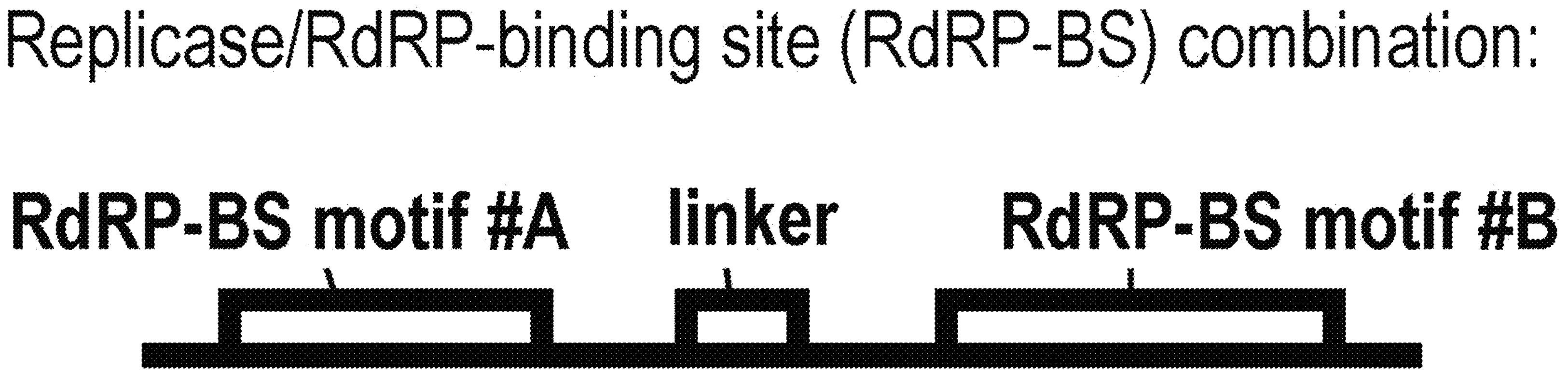

FIG. 7 shows the optimized design of a 5'-end or 3'-end RdRP-binding site (RdRP-BS) combination, respectively. In details, a 3~20-nucleotide linker sequence is placed between two RdRP-BS motifs (for example, motif #A and motif #B), wherein the linker sequence contains neither homology nor complementarity to the two RdRP-BS motif sequences. Also, the linker sequences of the 5'-end and 3'-end RdRP-BS combination may be the same or different from each other. Moreover, the two RdRP-BS motifs (e.g. motif #A and #B) in the same RdRP-BS combination may be either the same or different from each other. Furthermore, the two RdRP-BS motifs (e.g. motif #A and #B) in the same RdRP-BS combination may or may not contain either homology or complementarity, or both, to each other.

Figure 8:
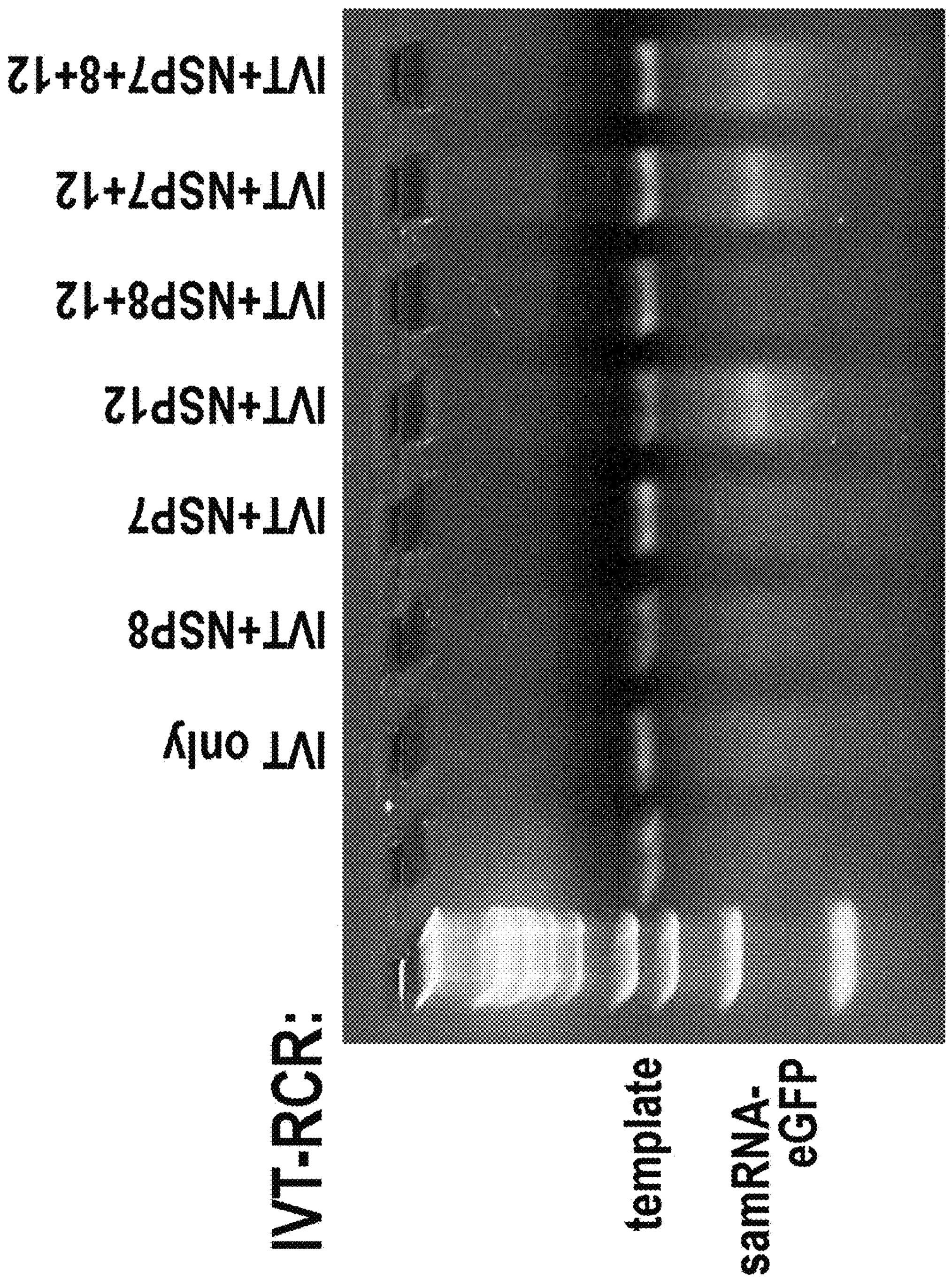

FIG. 8 shows the 2% agarose gel electrophoresis results of IVT-RCR using different coronaviral RdRP-NSP protein combinations in vitro. It clearly demonstrates that IVT-RCR reactions with addition of NSP12 protein show a significant increase of samRNA amplification compared to that of IVT only. However, the addition of NSP8 protein greatly diminishes this NSP12 effect of RdRP-mediated samRNA amplification, probably due to its primase function which may interfere with the de novo RNA synthesis activity of NSP12. Hence, RdRP-BS may be required for the de novo RNA synthesis function of NSP12, but not the primer-dependent RNA synthesis function of NSP8.

Figure 9:
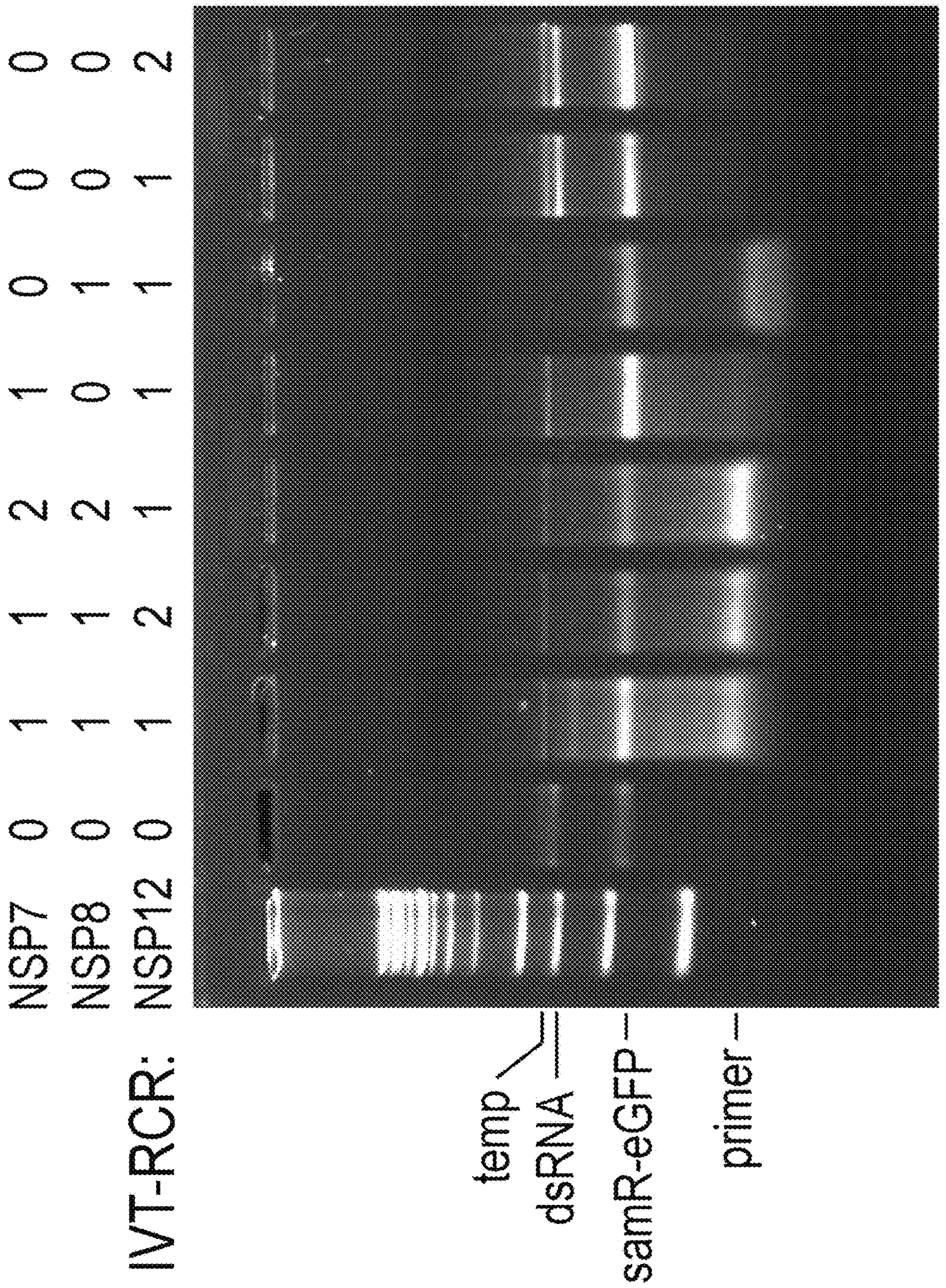

FIG. 9 shows the nondenaturing agarose gel electrophoresis results of IVT-RCR using different coronaviral RdRP-NSP protein combinations in vitro. In addition to the prior findings in FIG. 8, the results of FIG. 9 further demonstrate that NSP7 protein not only can enhance the samRNA amplification activity of NSP12 but also markedly reduce dsRNA formation in IVT-RCR, while the primase function of NSP8 protein however indeed interferes with the NSP12 RdRP activity in vitro.

Figure 10:
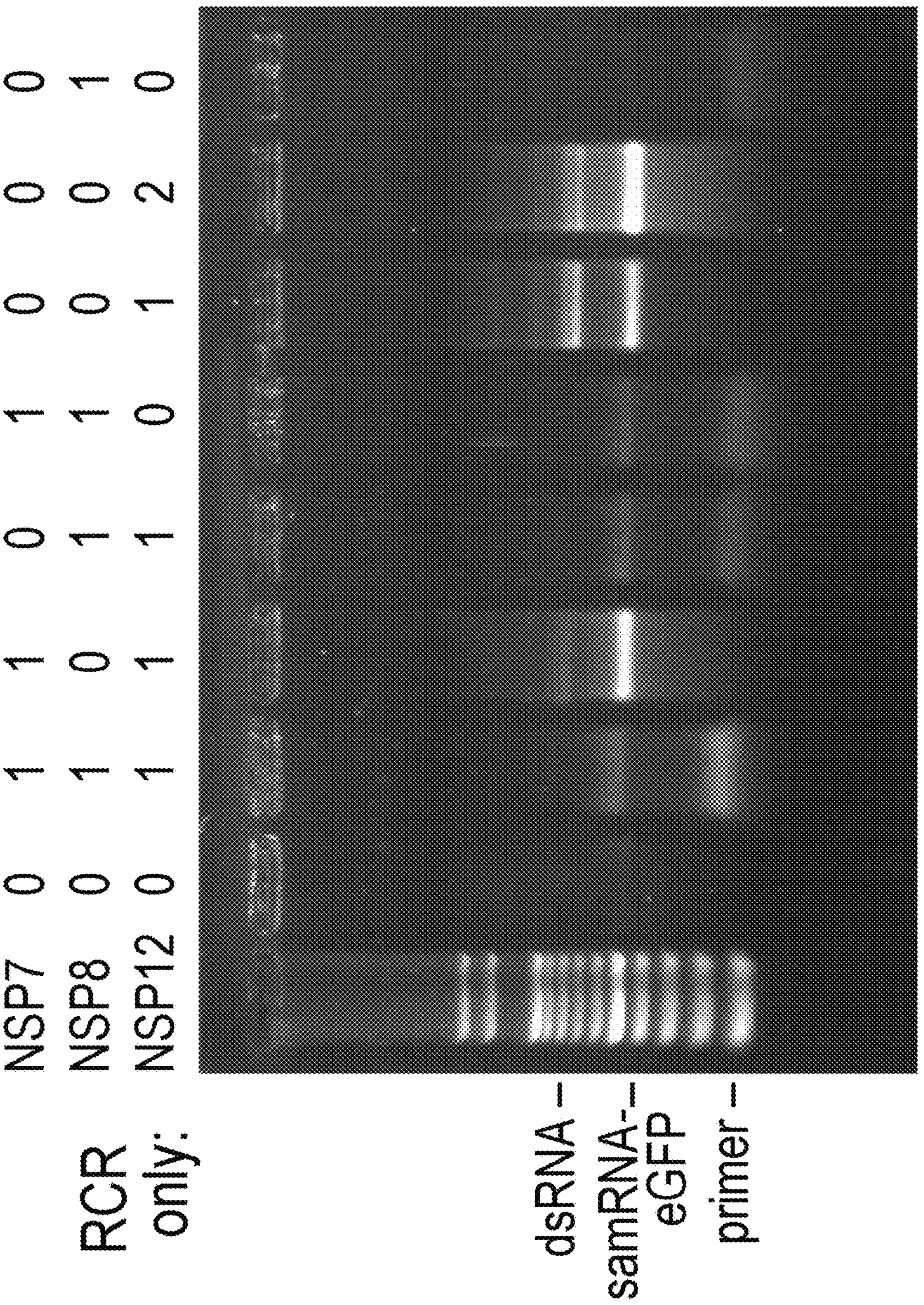

FIG. 10 shows the nondenaturing agarose gel electrophoresis results of RCR-based samRNA (e.g. eGFP samRNA) amplification using different combinations of coronaviral RdRP-NSP proteins in vitro. Similar to the results of FIG. 9, it clearly demonstrates that NSP12 is the core unit of replicase/RdRP enzymes responsible for samRNA amplification. Also, NSP7 protein not only can markedly enhance this NSP12 RdRP activity but also significantly reduce dsRNA formation in RCR, whereas NSP8 protein displays a strong primase function and interferes with the NSP12 RdRP activity in vitro.

Figure 11:
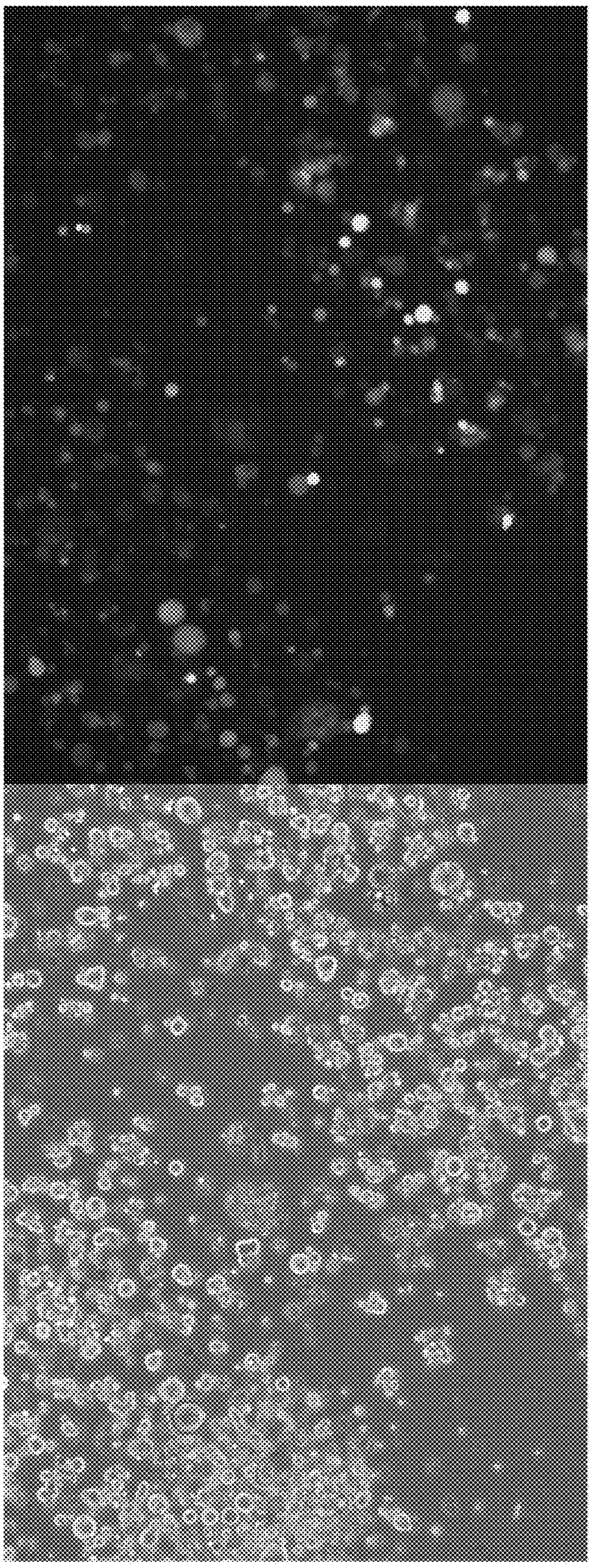

FIG. 11 shows the desired protein/peptide (e.g. eGFP) expression in the target cells of interest after co-transfection with a mixture of the designed samRNA platform template (e.g eGFP samRNA from FIG. 10) and NSP7+NSP12 mRNAs. For preventing possible interferon-associated immune response, all of the 5'-ends of the samRNA and NSP7+NSP12 mRNAs are preferably capped by m7G(5')ppp(5')N(m7G; cap-0) and/or its related cap (i.e. cap-1 or cap-2) analogs. Most preferably, the 5'-cap molecule is added by capping and/or cap modification enzymes, including but not limited to isolated, recombinant and/or modified coronaviral NSP12, NSP9/14, NSP10/16, and/or vaccinia capping enzyme as well as 2'-O-methyltransferase, or a combination thereof.

EXAMPLES

Human Cell Isolation and Cultivation

Starting tissue cells are obtained from either enzymatically dissociated skin cells using Aasen's protocol (*Nat. Protocols* 5, 371-382, 2010) or simply from the buffy coat fraction of heparin-treated peripheral blood cells. The isolated tissue samples must be kept fresh and used immediately by mixing with 4 mg/mL collagenase I and 0.25% TrypLE for 15-45 min, depending on cell density, and rinsed by HBSS containing trypsin inhibitor two times and then transferred to a new sterilized microtube containing 0.3 mL of feeder-free SFM culture medium (IrvineScientific, CA). After that, cells were further dissociated by shaking in a microtube incubator for 1 min at 37° C. and then transferred the whole 0.3 mL cell suspension to a 35-mm Matrigel-coated culture dish containing 1 mL of feeder-free SFM culture medium supplemented with formulated pre-miR-302+RdRp mRNA mixture, LIF, and bFGF/FGF2, or other optional defined factors. The concentrations of pre-miR-302+RdRp mRNA mixture, LIF, bFGF/FGF2, and other optional defined factors are ranged from 0.1 to 500 microgram (μg)/mL, respectively, in the cell culture medium. The cell culture medium and all of the supplements must be refreshed every 2-3 days and the cells are passaged at about 50%~60% confluence by exposing the cells to trypsin/EDTA for 1 min and then rinsing two times in HBSS containing trypsin inhibitor. For ASC expansion, the cells were replated at 1:5~1:500 dilution in fresh feeder-free MSC Expansion SFM culture medium supplemented with formulated pre-miR-302+RdRp mRNA mixture, LIF, bFGF/FGF2, and/or other optional defined factors. For culturing keratinocytes, cells are isolated from skin tissues and cultivated in EpiLife serum-free cell culture medium supplemented with human keratinocyte growth supplements (HKGS, Invitrogen, Carlsbad, CA) in the presence of proper antibiotics at 37° C. under 5% $CO_2$. Culture cells are passaged at 50%-60% confluency by exposing cells to trypsin/EDTA solution for 1 min and rinsing once with phenol red-free DMEM medium (Invitrogen), and the detached cells are replated at 1:10 dilution in fresh EpiLife medium with HKGS supplements. Human cancer and normal cell lines A549, MCF7, PC3, HepG2, Colo-829 and BEAS-2B were obtained either from the American Type Culture Collection (ATCC, Rockville, MD) or our collaborators and then maintained according to manufacturer's or provider's suggestions. After reprogramming, the resulting iPS cells (iPSCs) were cultivated and maintained following either Lin's feeder-free or Takahashi's feeder-based iPSC culture protocols (Lin et al., RNA 14:2115-2124, 2008; Lin et al., *Nucleic Acids Res.* 39:1054-1065, 2011; Takahashi K and Yamanaka S, *Cell* 126:663-676, 2006).

2. In-Vitro RNA Transfection

For intracellular delivery/transfection, 0.5~200 μg of RCR-amplified RNA/mRNA (e.g. pre-miR-302 or coronaviral S protein samRNA) and RdRp samRNA mixture (ratio ranged from about 200:1 to 1:200) is dissolved in 0.5 ml of fresh cell culture medium and mixed with 1-50 of In-VivoJetPEI or other similar transfection reagents. After 10~30 min incubation, the mixture is then added into a cell culture containing 50%~60% confluency of the cultivated cells. The medium is reflashed every 12 to 48 hours, depending on cell types. This transfection procedure may be performed repeatedly to increase transfection efficiency.

3. Preparation of RCR-Ready cDNA/samRNA Templates

Reverse transcription (RT) of desired RNA/mRNA is performed by adding about 0.01 ng~10 microgram (μg) of isolated RNA/mRNA into a 20~50 μL RT reaction (SuperScript III cDNA RT kit, ThermoFisher Scientific, MA, USA), following the manufacturer's suggestions. Depending on the RNA/mRNA amount, the RT reaction mixture further contains about 0.01~20 nmole RT primer, 0.1~10 mM each of deoxyribonucleoside triphosphate molecules (dNTPs; dATP, dTTP, dGTP and dCTP) and reverse transcriptase in 1× RT buffer. Then, the RT reaction is incubated at 37~65° C. for 1~3 hours (hr), depending on the length and structural complexity of the desired RNA/mRNA sequence(s), so as to form the complementary DNA (cDNA) of the desired RNA/mRNA which is then used for the next step of PCR. For isolation of coronaviral RdRp/helicase/methyltransferase mRNA/cDNA sequences, we have designed and used serval 3'-RT primers, including phosphorylated 5'-pCTGTAAGACT GTATGCGGTG TGTACATAGC-3' (SEQ ID NO:17) for generating NSP12 cDNA sequence, phosphorylated 5'-pTTGTAAGGTT GCCCTGTTGT CCAGCATTTC-3' (SEQ ID NO:18) for generating NSP7 cDNA sequence, phosphorylated 5'-pTTGTAGACGT ACTGTGGCAG CTAAACTACC AAG-3' (SEQ ID NO:19) for generating coronaviral NSP9 cDNA sequence, and phosphorylated 5'-pCTGAAGTCTT GTAAAAGTGT TCCAGAGGTT ATAAG-3'(SEQ ID NO:20) for generating coronaviral NSP14 cDNA sequence.

Next, polymerase chain reaction (PCR) is performed by adding about 0.01 pg~10 μg of the RT-derived cDNAs in a 20~50 μL PCR preparation mixture (High-Fidelity PCR master kit, ThermoFisher Scientific, MA, USA), following the manufacturer's suggestion. Then, the PCR mixture is incubated in twenty to thirty (20-30) cycles of denaturation at 94° C. for 30 sec~1 mim, annealing at 50~58° C. for 30 sec-J min, and then extension at 72° C. for 1~3 min, depending on the structure and length of the desired cDNA sequences, respectively. For example, the PCR primer pairs used are listed: phosphorylated 5'-forward primers including 5'-pATGCAATCGT TCTTAAACAG GGTTTGCG-3' (SEQ ID NO.21) and SEQ ID NO:17 for NSP12 cDNA, 5'-pATGAGTAAGA TGTCAGATGT AAAGTGCAC-3' (SEQ ID NO:22) and SEQ ID NO:18 for NSP7 cDNA, 5'-pATGAATAATG AGCTTAGTCC TGTTGCACTA CG-3' (SEQ ID NO:23) and SEQ ID NO:19 for NSP9, and 5'-pATGGCTGAAA ATGTAACAGG ACTCTTTAAA GATTG-3' (SEQ ID NO:24) and SEQ ID NO:20 for NSP14 cDNA. After that, using T4 DNA ligase, the resulting individual PCR products are respectively ligated to a pre-designed promoter-linked DNA sequence: 5'-TGAAGTAAAT AAAGGTAGCC TTAGCTAAAC GCGTGTAGAG AAGGAGACTA GTCCCTTTAG TGAGGGTTAA TTCATAAATA AATAAATAAA TAAATAAATA GATTGTAATA CGACTCACTA TAGCGCTCAA GGATCTCTTC TCTAATCTCG TAGCTAAGAC TTCTACGCCA CC-3' (SEQ ID NO:25), so as to form promoter-linked RdRP-BS-incorporated cDNA templates, respectively.

For generating various RCR-ready cDNA templates, another PCR reaction is performed under the same PCR condition, but using 0.1~10 μL of the above ligation products with another pair of pre-designed PCR primers including 5'-AGATTGTAAT ACGACTCACT ATAGCG-3' (SEQ ID NO:26) and 5'-GAATTAACCC TCACTAAAGG GACTAG-3' (SEQ ID NO:27). After further purification, the resulting PCR products are ready to serve as RCR-ready cDNA templates for both IVT and IVT-RCR. Notably, after IVT-RCR and/or RCR, a 5'-cap molecule, such as m7G(5')ppp(5')N(m7G; cap-0) and/or its related cap-1/cap-2 analogs, may be further incorporated into the resulting samRNA products, using coronaviral NSP12, NSP9/14, and/or NSP10/16 proteins, or a combination thereof.

For generating RCR-ready samRNA templates, an IVT-RCR reaction is then performed to generate the desired samRNA sequences from the RCR-ready cDNA templates, respectively. The IVT-RCR reaction contains 0.1 ng~10 μg of the RCR-ready cDNA template(s), 0.1~50 U each of isolated or recombinant replicase/RdRP enzymes, such as an individual or a mixture of isolated and/or modified coronaviral NSP12 (required), NSP7, NSP9, NSP14, and/or NSP10/16 proteins, or a combination thereof (BPS Bioscience, CA; Abcam, MA; Creative Enzymes, NY, USA), 0.1~4 mM each of modified and/or non-modified ribonucleoside triphosphate molecules (rNTPs; such as ATP, UTP, CTP, and GTP as well as their modified analogs), and RNA polymerases (i.e. T7, T3 and/or SP6) in 1× transcription buffer. The transcription buffer is commercially available for routine IVT practice and may be further optimized by adding or adjusting some additional factors suitable for RCR, including 10~400 mM Tris-HCL (pH 5~8 at 25° C.), 1~60 mM MgCl2, 1~60 mM Mn2+, 0.01~2 mM of GDP, 0.01~2 mM S-adenosyl methionine (SAM), and/or optional 0.001~10 mM of either betaine (trimethylglycine; TMG) or 3-(N-morpholino)propane sulfonic acid (MOPS), or a combination thereof. Then, the desired samRNA is produced by incubating the IVT-RCR reaction at 30-45° C. for 10 min-6 hr, depending on the stability and activity of the used replicase/RdRP and RNA polymerase enzymes. After RNase-free DNase digestion and further purification processes, the resulting IVT-RCR products can be directly used as RCR-ready samRNA templates for generating more samRNA molecules using the same optimized IVT-RCR reaction, but without the necessity of any T7, T3, or SP6 RNA polymerase. Notably, when using the mixture of NSP12, NSP7, NSP9/14, and/or NSP10/16 proteins in RCR or IVT-RCR, the resulting samRNA products are 5'-capped with either cap-0 or cap-1 structures, or both. Also, NSP12 protein may function to add a poly-A/U tail in the 3'-end of the resulting samRNA sequences.

4. Novel RCR Protocol

The RCR reaction contains about 0.01 ng~10 μg of the RCR-ready samRNA templates, about 0.1~50 U each of isolated or recombinant replicase/RdRP enzymes preferably containing a mixture of coronaviral NSP12 (required), NSP7, NSP9/14, and/or NSP10/16 proteins, or a combination thereof (BPS Bioscience, CA; Abcam, MA; Creative Enzymes, NY, USA), and 0.1~4 mM each of modified and/or non-modified ribonucleoside triphosphate molecules (rNTPs; such as ATP, UTP, CTP, and GTP as well as their modified analogs) in 1× optimized transcription buffer or called RCR buffer containing 10~400 mM Tris-HCL (pH 5~8 at 25° C.), 1~60 mM MgCl2, 1~60 mM Mn2+, 0.01~2 mM of GDP, 0.01~2 mM S-adenosyl methionine (SAM), 1~100 mM NaCl, 1~100 mM DTT (optional), and 1~20 mM spermidine (optional). Functionally, NSP12 is the core unit of coronaviral RdRP enzyme, while NSP7 and NSP13 are coronaviral helicases which facilitate the unwinding and prevention of dsRNA formation. Also, NSP9/14 and NSP10/16 are capping and methyltransferase enzymes, respectively, responsible for 5'-cap formation and specific cap-nucleotide methylation of the samRNA. Eventually, for samRNA amplification, the prepared RCR reaction is incubated at 25~45° C. for 10 min-6 hr, depending on the stability and activity of the used RdRP-NSP enzymes.

5. RNA Purification and Northern Blot Analysis

Desired RNAs (10 μg) are isolated with a mirVana™ RNA isolation kit (Ambion, Austin, TX) or similar purification filter column, following the manufacturer's protocol, and then further purified by using either 5%~10% TBE-urea polyacrylamide or 1%~3.5% low melting point agarose gel electrophoresis. For Northern blot analysis, the gel-fractionated RNAs are electroblotted onto a nylon membrane. Detection of the RNA and its IVT template (the PCR-derived cDNA product) is performed with a labeled [LNA]-DNA probe complementary to a target sequence of the desired RNA. The probe is further purified by high-performance liquid chromatography (HPLC) and tail-labeled with terminal transferase (20 units) for 20 min in the presence of either a dye-labeled nucleotide analog or [$^{32}$P]-dATP (>3000 Ci/mM, Amersham International, Arlington Heights, IL).

6. Protein Extraction and Western Blot Analysis

Cells ($10^6$) are lysed with a CelLytic-M lysis/extraction reagent (Sigma) supplemented with protease inhibitors, Leupeptin, TLCK, TAME and PMSF, following the manufacturer's suggestion. Lysates are centrifuged at 12,000 rpm for 20 min at 4° C. and the supernatant is recovered. Protein concentrations are measured using an improved SOFTmax protein assay package on an E-max microplate reader (Molecular Devices, CA). Each 30 μg of cell lysate are added to SDS-PAGE sample buffer under reducing (+50 mM DTT) and non-reducing (no DTT) conditions, and boiled for 3 min before loading onto a 6-8% polyacylamide gel. Proteins are resolved by SDS-polyacrylamide gel electrophoresis (PAGE), electroblotted onto a nitrocellulose membrane and incubated in Odyssey blocking reagent (Li-Cor Biosciences, Lincoln, NB) for 2 hr at room temperature. After that, a primary antibody is applied and mixed to the reagent and then together incubated at 4° C. After overnight incubation, the membrane is rinsed three times with TBS-T and then exposed to goat anti-mouse IgG conjugated secondary antibody to Alexa Fluor 680 reactive dye (1:2,000; Invitrogen-Molecular Probes), for 1 hr at the room temperature. After three additional TBS-T rinses, fluorescent scanning of the immunoblot and image analysis are conducted using Li-Cor Odyssey Infrared Imager and Odyssey Software v.10 (Li-Cor).

7. Immunostaining Assay

Cell/Tissue samples are first fixed in 100% methanol for 30 min at 4° C. and then 4% paraformaldehyde (in 1×PBS, pH 7.4) for 10 min at 20° C. After that, the samples are further incubated in 1×PBS containing 0.1%~0.25% Triton X-100 for 10 min and then washed in 1×PBS three times for 5 min. For immunostaining, corresponding primary antibodies were purchased from Invitrogen (CA, USA) and Sigma-Aldrich (MO, USA), respectively. Dye-labeled goat anti-rabbit or horse anti-mouse antibody are used as the secondary antibody (Invitrogen, CA, USA). Results are examined and analyzed at 100× or 200× magnification under a fluorescent 80i microscopic quantitation system with a Metamorph imaging program (Nikon).

8. In Vivo Transfection Assay

A mixture composition of desired samRNAs and RdRP-NSP mRNAs/samRNAs (weight ratio ranged from about 200:1 to 1:200) is further mixed with a proper amount of a delivery/transfection agent, such as an In-VivoJetPEI transfection reagent or other similar LNP-based delivery/transfection reagents, following the manufacturer's protocols, and then injected into blood veins or muscles of an animal, depending on the purpose of use. The delivery/transfection reagent is used for conjugating, encapsulating and/or formulating the samRNA and RdRP-NSP mRNA/samRNA mixture, so as to not only protect the RNA contents from degradation but also facilitate the delivery of the samRNA and RdRP-NSP mRNA/samRNA mixture into the specific target cells of interest in vitro, ex vivo, and/or in vivo.

9. Statistic Analysis

All data were shown as averages and standard deviations (SD). Mean of each test group was calculated by AVERAGE of Microsoft Excel. SD was performed by STDEV. Statistical analysis of data was performed by One-Way ANOVA. Tukey and Dunnett's t post hoc test were used to identify the significance of data difference in each group. $p<0.05$ was considered significant (SPSS v12.0, Claritas Inc).

REFERENCES

1. WO2002/092774 to Shi-Lung Lin et al.
2. U.S. Pat. No. 7,662,791 to Shi-Lung Lin et al.
3. U.S. Pat. No. 8,080,652 to Shi-Lung Lin et al.
4. U.S. Pat. No. 8,372,969 to Ying SY and Shi-Lung Lin.
5. U.S. Pat. No. 8,609,831 to Shi-Lung Lin and Ying SY.
6. Shi-Lung Lin and Ji H; cDNA library construction using in-vitro transcriptional amplification. *Methods Mol Biol.* 221:93-101, 2003.
7. Ahn et al.; Biochemical characterization of a recombinant SARS coronavirus nsp12 RNA-dependent RNA polymerase capable of copying viral RNA templates. *Arch. Virol.* 157:2095-2104, 2012.
8. Bloom et al; Self-amplifying RNA vaccines for infectious diseases. *Gene Therapy* 28:117-129, 2021.
9. Hyde et al.; The 5' and 3' ends of alphavirus RNAs—Non-coding is not non-functional. *Virus Research* 206: 99-107, 2015.
10. McDowell et al.; Determination of intrinsic transcription termination efficiency by RNA polymerase elongation rate. *Science* 266:822-825, 1994.
11. Aasen et al.; Isolation and cultivation of human keratinocytes from skin or plucked hair for the generation of induced pluripotent stem cells. *Nat. Protocols* 5:371-382, 2010.
12. Shi-Lung Lin et al.; Mir-302 reprograms human skin cancer cells into a pluripotent ES-cell-like state. RNA 14:2115-2124, 2008.
13. Shi-Lung Lin et al.; Regulation of somatic cell reprogramming through inducible mir-302 expression. *Nucleic Acids Res.* 39:1054-1065, 2011.
14. Takahashi K and Yamanaka S; Induction of pluripotent stem cells from mouse embryonic and adult fibroblast cultures by defined factors. *Cell* 126:663-676, 2006.
15. Hillen et al.; Structure of replicating SARS-CoV-2 polymerase. *Nature* 584:154-159, 2020.
16. U.S. Pat. No. 11,291,635 to Geall et al.
17. U.S. Pat. No. 11,504,421 to Blair et al.
18. U.S. Pat. No. 11,510,973 to Blair et al.

The invention claimed is:

1. A novel self-amplifying RNA (samRNA) composition, comprising: At least an RNA sequence flanked with at least a 5'-end RdRP-binding site and at least a 3'-end RdRP-binding site; wherein said 5'-end RdRP-binding site and said 3'-end RdRP-binding site contains:

(i) at least a SEQ ID NO:13 and at least a SEQ ID NO:14 sequence and the SEQ ID NO: 13 and SEQ ID NO:14 are separated by a 3~20-nucleotide linker sequence which is neither homologous nor complementary to the SEQ ID NO: 13 and SEQ ID NO: 14; or (ii) at least a SEQ ID NO:15 and at least a SEQ ID NO: 16 sequence and the SEQ ID NO: 15 and SEQ ID NO:16 are separated by another 3~20-nucleotide linker sequence which is neither homologous nor complementary to the SEQ ID NO:15 and SEQ ID NO: 16;

wherein said 5'-end RdRP-binding site and said 3'-end RdRP-binding site are different.

2. The composition as defined in claim 1, wherein said RNA sequence is non-coding RNA.

3. The composition as defined in claim 1, wherein said RNA sequence is protein-/peptide- or antibody-coding mRNA.

4. The composition as defined in claim 1, wherein said RNA sequence is in either single-stranded or double-stranded conformation.

5. The composition as defined in claim 1, wherein said RNA sequence further contains modified nucleotide analogs.

6. The composition as defined in claim 1, wherein said RNA sequence further contains at least a kozak motif, poly-A signal, and poly-A tail.

7. The composition as defined in claim 1, wherein said RNA sequence is a pharmaceutical compound or composition.

8. The composition as defined in claim 1, wherein said 5'-end RdRP-binding site contains at least the SEQ ID NO:13 and at least the SEQ ID NO: 14 sequence and the SEQ ID NO: 13 and SEQ ID NO: 14 are separated by the 3~20-nucleotide linker sequence which is neither homologous nor complementary to the SEQ ID NO: 13 and SEQ ID NO: 14; and said 3'-end RdRP-binding site contains at least the SEQ ID NO:15 and at least the SEQ ID NO: 16 sequence and the SEQ ID NO:15 and SEQ ID NO: 16 are separated by the 3~20-nucleotide linker sequence which is neither homologous nor complementary to the SEQ ID NO: 15 and SEQ ID NO: 16.

9. The composition as defined in claim 1, wherein said 5'-end RdRP-binding site contains at least the SEQ ID NO:15 and at least the SEQ ID NO:16 sequence and the SEQ ID NO:15 and SEQ ID NO:16 are separated by the 3~20-nucleotide linker sequence which is neither homologous nor complementary to the SEQ ID NO: 15 and SEQ ID NO: 16; and said 3'-end RdRP-binding site contains at least the SEQ ID NO:13 and at least the SEQ ID NO:14 sequence and the SEQ ID NO:13 and SEQ ID NO:14 are separated by the 3~20-nucleotide linker sequence which is neither homologous nor complementary to the SEQ ID NO: 13 and SEQ ID NO: 14.

10. The composition as defined in claim 1, further comprising a delivery agent for facilitating intracellular transfection in vitro, ex vivo as well as in vivo.

11. The composition as defined in claim 10, wherein said delivery agent is liposomal nanoparticles (LNP).

12. The composition as defined in claim 1, wherein said samRNA composition further contains 5'-cap molecule, such as m7G.

13. The composition as defined in claim 1, wherein said samRNA composition further contains a 3'-cap molecule selected from 5'-phosphorothioate-uridine (PU), 5'-phosphoadenosine 3'-phosphate (PAP), and adenosine 3'-phosphate 5'-phosphosulfate (PAPS).

14. The composition as defined in claim 1, wherein said samRNA composition encodes at least an antibody.

15. The composition as defined in claim 1, wherein said samRNA composition encodes precursor microRNA (pre-miRNA).

16. The composition as defined in claim 1, wherein said samRNA composition encodes short hairpin RNA (shRNA).

17. The composition as defined in claim 1, wherein said samRNA composition contains modified uridine nucleotides selected from pseudouridine, methyluridine, methoxyuridine, or the related modified analogs.

18. A pharmaceutical compound or composition comprising the samRNA composition as defined in claim 1.

* * * * *

SEQUENCE LISTING

```
Sequence total quantity: 27
SEQ ID NO: 1            moltype =   length =
SEQUENCE: 1
000

SEQ ID NO: 2            moltype =   length =
SEQUENCE: 2
000

SEQ ID NO: 3            moltype =   length =
SEQUENCE: 3
000

SEQ ID NO: 4            moltype =   length =
SEQUENCE: 4
000

SEQ ID NO: 5            moltype =   length =
SEQUENCE: 5
000

SEQ ID NO: 6            moltype =   length =
SEQUENCE: 6
000

SEQ ID NO: 7            moltype =   length =
SEQUENCE: 7
000

SEQ ID NO: 8            moltype =   length =
SEQUENCE: 8
000

SEQ ID NO: 9            moltype =   length =
SEQUENCE: 9
000

SEQ ID NO: 10           moltype =   length =
SEQUENCE: 10
000

SEQ ID NO: 11           moltype =   length =
SEQUENCE: 11
000

SEQ ID NO: 12           moltype =   length =
SEQUENCE: 12
000

SEQ ID NO: 13           moltype = RNA  length = 14
FEATURE                 Location/Qualifiers
source                  1..14
                        mol_type = other RNA
                        organism = Synthetic construct
variation               3..4
                        note = Y=C or U. Y is exchangable with R. R=A or G.
variation               9..10
                        note = Y=C or U. Y is exchangable with R. R=A or G.
variation               6
                        note = S is G or C.
variation               14
                        note = R=A or G. G is exchangable with Y. Y=C or U.
SEQUENCE: 13
gayytsttyy ctar                                                       14

SEQ ID NO: 14           moltype = RNA  length = 14
FEATURE                 Location/Qualifiers
source                  1..14
                        mol_type = other RNA
                        organism = Synthetic construct
variation               1
                        note = R=A or G. G is exchangable with Y. Y=C or U.
variation               5..6
                        note = Y=C or U. Y is exchangable with R. R=A or G.
variation               9
                        note = S is G or C.
variation               11..12
                        note = Y=C or U. Y is exchangable with R. R=A or G.
```

```
SEQUENCE: 14
rtagyyaasa yytc                                                    14

SEQ ID NO: 15          moltype = RNA  length = 14
FEATURE                Location/Qualifiers
source                 1..14
                       mol_type = other RNA
                       organism = Synthetic construct
variation              3..4
                       note = R=A or G. G is exchangable with Y. Y=C or U.
variation              6
                       note = S is G or C.
variation              9..10
                       note = R=A or G. G is exchangable with Y. Y=C or U.
variation              14
                       note = Y=C or U. Y is exchangable with R. R=A or G.
SEQUENCE: 15
gtrrcsttrr ctay                                                    14

SEQ ID NO: 16          moltype = RNA  length = 14
FEATURE                Location/Qualifiers
source                 1..14
                       mol_type = other RNA
                       organism = Synthetic construct
variation              1
                       note = Y=C or U. Y is exchangable with R. R=A or G.
variation              5..6
                       note = R=A or G. G is exchangable with Y. Y=C or U.
variation              9
                       note = S is G or C.
variation              11..12
                       note = R=A or G. G is exchangable with Y. Y=C or U.
SEQUENCE: 16
ytagrraasg rrac                                                    14

SEQ ID NO: 17          moltype = DNA  length = 30
FEATURE                Location/Qualifiers
misc_feature           1..30
                       note = Synthetic
source                 1..30
                       mol_type = other DNA
                       organism = Synthetic construct
SEQUENCE: 17
ctgtaagact gtatgcggtg tgtacatagc                                   30

SEQ ID NO: 18          moltype = DNA  length = 30
FEATURE                Location/Qualifiers
misc_feature           1..30
                       note = Synthetic
source                 1..30
                       mol_type = other DNA
                       organism = Synthetic construct
SEQUENCE: 18
ttgtaaggtt gccctgttgt ccagcatttc                                   30

SEQ ID NO: 19          moltype = DNA  length = 33
FEATURE                Location/Qualifiers
misc_feature           1..33
                       note = Synthetic
source                 1..33
                       mol_type = other DNA
                       organism = Synthetic construct
SEQUENCE: 19
ttgtagacgt actgtggcag ctaaactacc aag                               33

SEQ ID NO: 20          moltype = DNA  length = 35
FEATURE                Location/Qualifiers
misc_feature           1..35
                       note = Synthetic
source                 1..35
                       mol_type = other DNA
                       organism = Synthetic construct
SEQUENCE: 20
ctgaagtctt gtaaaagtgt tccagaggtt ataag                             35

SEQ ID NO: 21          moltype = DNA  length = 28
FEATURE                Location/Qualifiers
misc_feature           1..28
                       note = Synthetic
```

-continued

```
source                  1..28
                        mol_type = other DNA
                        organism = Synthetic construct
SEQUENCE: 21
atgcaatcgt tcttaaacag ggtttgcg                                  28

SEQ ID NO: 22           moltype = DNA  length = 29
FEATURE                 Location/Qualifiers
misc_feature            1..29
                        note = Synthetic
source                  1..29
                        mol_type = other DNA
                        organism = Synthetic construct
SEQUENCE: 22
atgagtaaga tgtcagatgt aaagtgcac                                 29

SEQ ID NO: 23           moltype = DNA  length = 32
FEATURE                 Location/Qualifiers
misc_feature            1..32
                        note = Synthetic
source                  1..32
                        mol_type = other DNA
                        organism = Synthetic construct
SEQUENCE: 23
atgaataatg agcttagtcc tgttgcacta cg                             32

SEQ ID NO: 24           moltype = DNA  length = 35
FEATURE                 Location/Qualifiers
misc_feature            1..35
                        note = Synthetic
source                  1..35
                        mol_type = other DNA
                        organism = Synthetic construct
SEQUENCE: 24
atggctgaaa atgtaacagg actctttaaa gattg                          35

SEQ ID NO: 25           moltype = DNA  length = 172
FEATURE                 Location/Qualifiers
misc_feature            1..172
                        note = Synthetic
source                  1..172
                        mol_type = other DNA
                        organism = Synthetic construct
SEQUENCE: 25
tgaagtaaat aaaggtagcc ttagctaaac gcgtgtagag aaggagacta gtccctttag  60
tgagggttaa ttcataaata aataaataaa taaataaata gattgtaata cgactcacta  120
tagcgctcaa ggatctcttc tctaatctcg tagctaagac ttctacgcca cc         172

SEQ ID NO: 26           moltype = DNA  length = 26
FEATURE                 Location/Qualifiers
misc_feature            1..26
                        note = Synthetic
source                  1..26
                        mol_type = other DNA
                        organism = Synthetic construct
SEQUENCE: 26
agattgtaat acgactcact atagcg                                    26

SEQ ID NO: 27           moltype = DNA  length = 26
FEATURE                 Location/Qualifiers
misc_feature            1..26
                        note = Synthetic
source                  1..26
                        mol_type = other DNA
                        organism = Synthetic construct
SEQUENCE: 27
gaattaaccc tcactaaagg gactag                                    26
```